United States Patent [19]
Thomas et al.

[11] Patent Number: 5,857,462
[45] Date of Patent: *Jan. 12, 1999

[54] SYSTEMATIC WAVELENGTH SELECTION FOR IMPROVED MULTIVARIATE SPECTRAL ANALYSIS

[75] Inventors: Edward V. Thomas; Mark R. Robinson; David M. Haaland, all of Albuquerque, N. Mex.

[73] Assignee: Sandia Corporation, Albuquerque, N. Mex.

[*] Notice: The term of this patent shall not extend beyond the expiration date of Pat. No. 5,435,309.

[21] Appl. No.: 505,829

[22] Filed: Jul. 24, 1995

Related U.S. Application Data

[63] Continuation of Ser. No. 104,857, Aug. 10, 1993, Pat. No. 5,435,309.

[51] Int. Cl.$^6$ ........................................................ A61B 5/00
[52] U.S. Cl. .............................................................. 128/633
[58] Field of Search ................................ 128/633, 664–7; 359/39–41

[56] References Cited

U.S. PATENT DOCUMENTS

| | | |
|---|---|---|
| 4,883,963 | 11/1989 | Kemeny et al. . |
| 5,120,961 | 6/1992 | Levin et al. . |
| 5,337,745 | 8/1994 | Benaron ................................. 128/633 |
| 5,353,790 | 10/1994 | Jacques et al. ......................... 128/633 |
| 5,377,674 | 1/1995 | Kuestner ................................. 128/633 |

OTHER PUBLICATIONS

"Reagentless Near–Infrared Determinationo of Glucose in Whole Blooding Using Multvariate Calibration", David M. Haaland, et al., *Applied Spectroscopy*, vol. 46, No. 1992, pp. 1575–1578.

"Monte Carlo Study of the Effect of Noise on Wavelength Selection During Computerized Wavelength Searches", Howard Mark, *Applied Spectroscopy*, vol. 42, No. 8, 1988, pp. 1427–1440.

"Global Optimization by Simulated Annealing with Wavelength Selection for Ultraviolet–Visible Spectrophotometry", *Analytical Chemistry*, vol. 61, No. 18, Sep. 15, 1989, pp. 2024–2030.

"Noninvasive Blood Glucose Assay by Near–Infrared Diffuse Reflectance Spectroscopy of the Human Inner Lip", R Marbach, et al., *Applied Spectroscopy*, vol. 47, No. 7, 1993, pp. 875–881.

(List continued on next page.)

*Primary Examiner*—Jennifer Bahr
*Assistant Examiner*—Bryan K. Yarnell
*Attorney, Agent, or Firm*—Dewitt M. Morgan; Kevin Lynn Wildenstein

[57] ABSTRACT

Methods and apparatus for determining in a biological material one or more unknown values of at least one known characteristic (e.g. the concentration of an analyte such as glucose in blood or the concentration of one or more blood gas parameters) with a model based on a set of samples with known values of the known characteristics and a multivariate algorithm using several wavelength subsets. The method includes selecting multiple wavelength subsets, from the electromagnetic spectral region appropriate for determining the known characteristic, for use by an algorithm wherein the selection of wavelength subsets improves the model's fitness of the determination for the unknown values of the known characteristic. The selection process utilizes multivariate search methods that select both predictive and synergistic wavelengths within the range of wavelengths utilized. The fitness of the wavelength subsets is determined by the fitness function F=f (cost, performance). The method includes the steps of: (1) using one or more applications of a genetic algorithm to produce one or more count spectra, with multiple count spectra then combined to produce a combined count spectrum; (2) smoothing the count spectrum; (3) selecting a threshold count from a count spectrum to select these wavelength subsets which optimize the fitness function; and (4) eliminating a portion of the selected wavelength subsets. The determination of the unknown values can be made: (1) noninvasively and in vivo; (2) invasively and in vivo; or (3) in vitro.

7 Claims, 14 Drawing Sheets

OTHER PUBLICATIONS

"Chemometrics and spectral frequency selection", Philip J. Brown, et al., *Phil. Trans. R. Soc. Lond.,* A (1991) 337, pp. 311–322.

Evaluation of Experimental Designs for Multicomponent Determinations by Spectrophotometry, L.L. John, et al., *Analytica Chimica Acta,* 207, (1988) pp. 125–135.

"Partial Least–Squares Methods for Spectral Analyses. 1. Relation to Other Quantitative Calibration Methods and the Extraction of Qualitative Information", David M. Haaland, et al., *Analytical Chemisty,* 1988, 60, pp. 1193–1202.

"Genetic algorithms for large–scale optimization in chemometrics: an application", C. B. Lucasius, et al., *Trends in Analytical Chemistry,* vol. 10, No. 8, 1991, pp. 254–261.

"Optimization of calibration data with the dynamic genetic algorithm", Tong–Hua Li, *Analytica Chemica Acta,* 268 (1992), pp. 123–134.

"Wavelength Selection in Multicomponent Near–Infrared Calibration", Philip J. Brown, *Journal of Chemometrics,* vol. 6, pp.151–161 (1992).

"Genetic Algorithms and the Optimal Allocation of Trials", John H. Holland, *SIAM J. Comput.,* vol. 2, No. 2, Jun. 1973.

"Cross–validatory Choice and Assessment of Statistical Predictions" M. Stone, paper given before Royal Statistical Society, Research Section, Dec. 5, 1973.

"Post–Prandial Blood Glucose Determinaton by Quantitative Mid–Infrared Spectroscopy", Kenneth J. Ward, et al., *Applied Spectroscopy,* vol. 46, No. 6, 1992, pp. 959–965.

"Nonivasive Glucose Monitoring in Diabetic Patients: A preliminary Evaluation", M. Ries Robinson, et al., *Clinical Chemistry,* vol. 38, No. 9, 1992, pp. 1618–1622.

"Acousto–Optic Devices, Optical Elements for Spectroscopy", Chieu D. Tran, *Analytical Chemistry,* vol. 64, No. 20, Oct. 15, 1992, pp. 971A–981A.

"Defense–Related Acousto–Optics Transform Commerical Products", Ronald G. Rosemeier, *Photonics Spectra,* (1985) 34, No. 2, pp. 114–120.

"Comparison of Linear Statistical Methods for Calibraton of NIR Instruments ", T. Naes, et al., *Applied Statistics,* (1986) 35 No. 2, pp. 195–206.

"Continuum Regression: Cross–validated Sequentially Constructed Prediction Embracing Ordinary Least Squares, Partial Least Squares and Principal Components Regression", M. Stone, J. R. Statist. Soc. B (1990) 52, No. 2, pp. 237–269.

"Errors–in–Variables Estimation in Multivariate Calibration", Edward V. Thomas, Technometrics, Nov. 1991, vol. 33, No. 4, pp. 405–413.

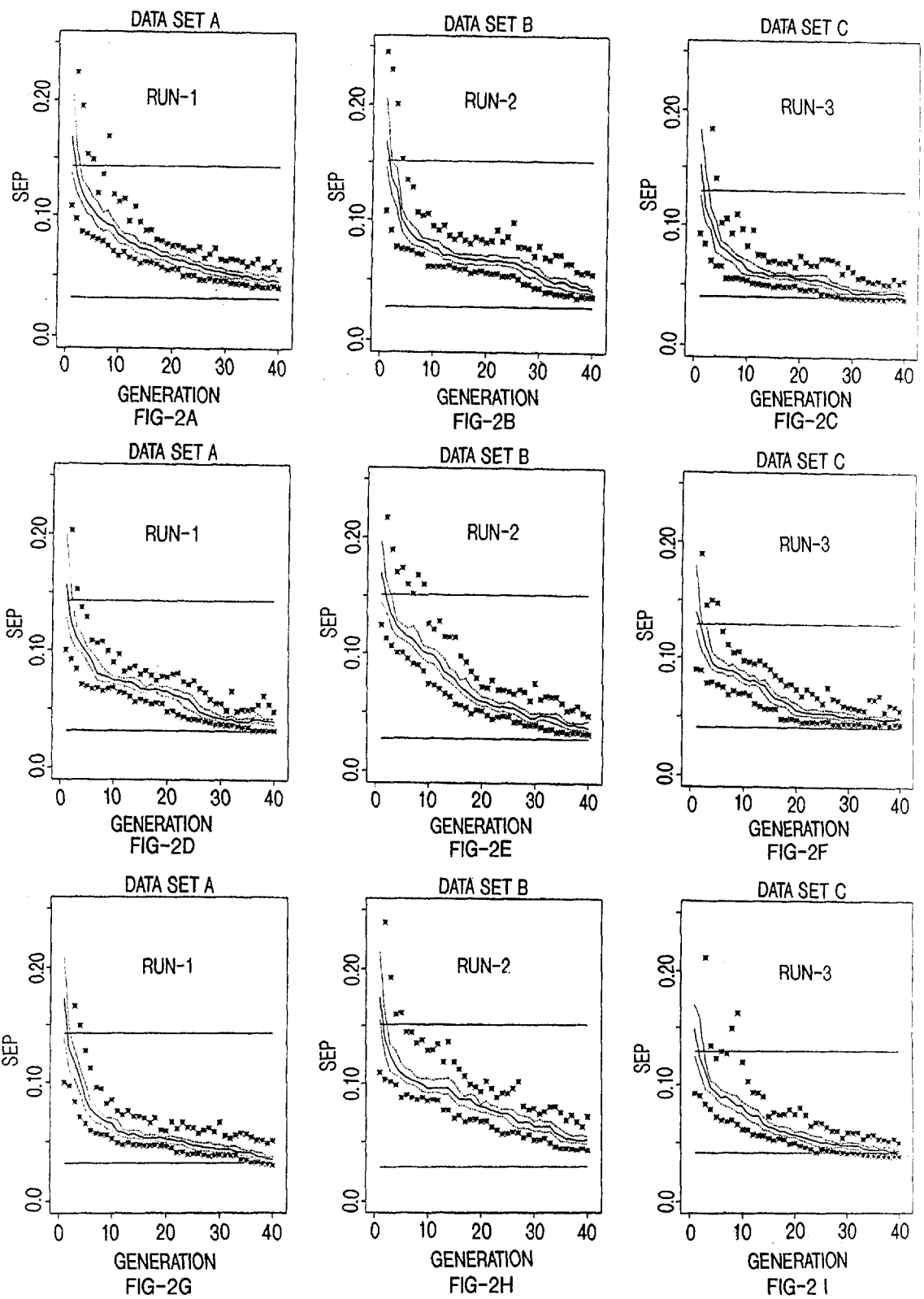

5,857,462

SYSTEMATIC WAVELENGTH SELECTION FOR IMPROVED MULTIVARIATE SPECTRAL ANALYSIS

This is a continuation of application Ser. No. 08/104,857 filed on Aug. 10, 1993, now U.S. Pat. No. 5,435,309.

BACKGROUND OF THE INVENTION

This invention relates to instrumentation and related methodology for determining, primarily in a biological material, one or more unknown values of a known characteristic (e.g., the concentration of an analyte such as glucose in blood, or the concentration of at least one blood gas parameter) with a model based on a set of samples with known analyte values and a multivariate algorithm. In addition to glucose, blood analytes include alcohol, fatty acids, cholesterol, lipoproteins, triglycerides, white blood cells, hematocrit, hemoglobin, blood urea nitrogen, creatinine, bilirubin, and electrolytes. The instrument maximizes performance while simultaneously minimizing cost. Minimization of cost and maximization of performance are obvious goals, yet consideration of both in a systematic fashion is difficult. The ability to perform both objectives is especially difficult when designing complex optical instrumentation using multivariate quantitative spectroscopy. Such a capability is even more critical when designing noninvasive medical instrumentation due to the significant ramifications associated with spurious results and the cost containment measures being introduced throughout the medical profession.

Multivariate calibration techniques, such as principal component regression (PCR) and partial least squares regression (PLS), have proven to be useful in conjunction with spectral measurements, allowing for quantitative analysis of materials and material properties in various forms (gases, liquids, and solids) in an ever growing number of applications. Applications include nondestructively determining the composition of passivation glass deposited on wafers during the fabrication of semiconductor devices and noninvasively determining the concentration of glucose in human blood (as set forth in U.S. Pat. No. 4,975,581).

In spectroscopic applications, measurements such as absorbance and reflectance, are taken at one or more spectral wavelengths. These measurements are obtained from a number of specimens in which the amount of the analyte of interest (e.g. glucose, alcohol, and arterial blood gasses) has been determined by some independent assay (e.g., wet chemistry). Together, the spectral measurements and results from the independent assays are used to construct empirical calibration models that relate the amount of the analyte of interest to the spectral measurements. These models are then used to predict analyte concentrations of future samples solely on the basis of the spectral measurements. Quantitative analysis based on spectral data has advantages over some of the more traditional methods of analysis because it is often much quicker, less labor intensive (hence cheaper), and can be nondestructive and/or noninvasive.

The basis for the many calibration models using absorbance spectroscopy is Beer's Law. In the limiting case of dilute component concentrations in a nonabsorbing medium, the absorbance of a sample at wavelength $\lambda$, $y(\lambda)$, depends upon the concentration of the multiple (p) chemical species in the sample through Beer's Law, which is $$y(\lambda) = a_\lambda + x_1 k_1(\lambda) + x_2 k_2(\lambda) + \ldots + x_p k_p(\lambda) + e_\lambda, \quad \text{[Equation 1]}$$

where $a_\lambda$ is a spectral intercept, $x_i$ is the concentration of the $i^{th}$ chemical species, $k_i(\lambda)$ is the product of the optical pathlength with the absorptivity of the $i^{th}$ chemical species, and $e_\lambda$ is the measurement error of the absorbance at wavelength $\lambda$. The degree to which Beer's Law is adhered to depends on the nature of the sample components, the concentrations of the chemical components as well as the wavelength considered. The performance of calibration methods is best when Beer's Law provides a good approximation over the range of wavelengths used.

There has been a rapid evolution of multivariate calibration methods for analysis of spectral data due to the availability of advanced computerized optical instrumentation. Early on, spectroscopists used methods based on a single wavelength to develop a calibration model. However, the usefulness of these methods, known as univariate methods, is limited to cases where the spectral response of the analyte of interest is isolated from that of other components in the material to be analyzed, or the spectral response of the analyte dominates that of other spectrally absorbing components. (Note: as typically used herein, analyte refers to the component in the system to be analyzed, even though there are other components present in the system and substitute therefore—In addition to glucose, blood analytes include alcohol, fatty acids, cholesterol, lipoproteins, triglycerides, white blood cells, hematocrit, hemoglobin, blood urea nitrogen, creatinine, bilirubin, and electrolytes.) Multivariate calibration models relating an analyte's concentration to a linear combination of measurements from several wavelengths were introduced in order to develop models that are useful in a broader range of conditions; specifically to include cases where the spectral features of the analyte are overlapped with features of other components in the material to be analyzed. However, the success of these techniques generally requires wavelength selection based on specific knowledge of the spectra of interfering components in the sample material as well as that of the analyte.

Recently, calibration methods (e.g., PLS) capable of simultaneously using measurements from a very large number of wavelengths, sometimes identified as full-spectrum methods, have been introduced. These methods, which are capable of analyzing rather complex materials, have a number of inherent advantages (e.g., signal averaging and improved outlier detection) over methods that use relatively few wavelengths. While still allowing for overlapped spectra of various components, the capability of using many wavelengths seemingly eliminates the need for wavelength selection and the implicit requirement of knowledge of the spectra of interfering components. The number of potential spectral wavelengths available to use with a full-spectrum method is often very large, perhaps thousands. Thus, with full-spectrum methods, spectroscopists often use all available wavelengths within some broad range. However, in many applications, measurements from a large number of the spectral wavelengths are irrelevant or difficult to incorporate in a model because of non-linearities. While fill-spectrum methods like PLS are able to accommodate non-linearities to some degree, inclusion of irrelevant (or difficult) spectral measurements in a model can seriously degrade performance.

Difficult or irrelevant spectral sections are sometimes removed through a spectral "pre-treatment" step. In such a pre-treatment step subject matter knowledge can be used to remove regions which exhibit the following characteristics: (1) regions which lack spectral information; (2) regions of significant non-linearity; and (3) regions with a poor signal-to-noise ratio. This type of simple processing is well known and has been previously used. See Haaland, et al., "Reagentless Near-infrared determination of glucose in whole blood using multivariate calibration", *Applied Spectroscopy*, Vol. 46, Nov. 10, 1992. In the experiment performed in the above reference, "The spectral region between 4850 and 6600 cm$^1$ is a water band that is too strongly absorbing and too variable in intensity to aid in the analysis".

In many and probably most situations where full-spectrum methods are utilized, practitioners often use all wavelengths. Wavelength selection is not recommended or deemed necessary as evidenced by:

1. Howard Mark, "A Computerized Study of the Effect of Noise on Wavelength Selection during Computerized Wavelength Searches," *Applied Spectroscopy*, 42, 1427–1440 (1988): "Currently there is a trend toward use of calibration methods, such a Principal Component Analysis (PCA) and Partial Least Squares (PLS), that do not require wavelength selection because data at all available wavelengths are used."
2. John H. Kalivas, Nancy Roberts, and Jon M. Sutter, "Global Optimization by Simulated Annealing with Wavelength Selection for Ultraviolet-Visible Spectrophotometry," *Analytical Chemistry*, 61, 2024–2030 (1989): "Two of the most common techniques used in spectral chemical analysis are principal components regression (PCR) and partial least squares (PLS). Even though wavelength searches are not necessary, the proper number of factors to include in an analysis must be established, which represents a computational search as well."

With advice such as the foregoing, practitioners often use full spectrum methods in conjunction with all wavelengths within some broad range. For example, in a very recent peer reviewed paper on the noninvasive analysis of blood glucose, Marbach, et al., "Noninvasive Blood Glucose Assay by Near-Infrared Diffuse Reflection Spectroscopy of the Human Inner Lip," Applied Spectroscopy, 47, pp. 875–881 (1993), the authors use all wavelengths in a very wide spectral range. Thus, it is clear that even leading researchers in the field on noninvasive glucose measurement do not recognize the potential benefits of using wavelength selection in conjunction with full-spectrum methods.

In relatively simple cases involving materials with only a few components, spectroscopists can sometimes select wavelength regions for analysis based on knowledge of where the components are spectrally active and likely to follow Beer's Law. However, when analyzing materials of a more complex nature (e.g., human tissue or other biological material), wavelength selection is much more difficult. There are a number of reasons for this. First, some of the material components may be unknown. This is especially true in noninvasive applications where the entire molecular structure of the biological material (e.g., finger) is not known. Furthermore, even if a component is known, its characteristic spectral signature may be modified by variable experimental conditions (e.g., temperature) and the host medium. Even if all components along with their associated spectral signatures are known, considerable spectral overlap among different components (such as found in the near-infrared region among, for instance, glucose, urea, blood urea nitrogen (BUN), alcohol, and cholesterol) can make wavelength selection very difficult. Physical and chemical interactions among components, along with other sources of deviations from Beer's Law, also impede the ability to select wavelengths.

Commonly used approaches given for wavelength selection in complex situations are based on criteria that do not utilize the interrelationships among measurements at multiple spectral wavelengths. See Hruschka, W. R., "Data Analysis: Wavelength Selection Methods," in *Near-Infrared Technology in the Agricultural and Food Industries*, (Williams, P., and Norris K. editors), American Association of Cereal Chemists, Inc., St. Paul, Minn. (1987), and Brown, P. J., Spiegelman, C. H., and Denham, M. C., "Chemometrics and Spectral Frequency Selection," *Philosophical Transactions of the Royal Society of London, Series A*, 337, 311–322 (1991). By not considering the interrelationships among measurements, these methods will miss synergistic effects that could ultimately have significant positive effects on model performance.

Thus, for complex problems such as the measurement of blood analytes, (such as glucose, alcohol, fatty acids, cholesterol, lipoproteins, triglycerides, white blood cells, hematocrit, hemoglobin, blood urea nitrogen, creatinine, bilirubin, and electrolytes there is a fundamental need for development of systematic wavelength selection that uses the interrelationships among measurements. Such a systematic and reliable procedure for wavelength selection dramatically improves the performance of these full spectrum methods and greatly broadens their use to more complex problems.

To demonstrate the need for wavelength or frequency selection when using full-spectrum methods such as PLS, consider a simple hypothetical chemical system with a single spectrally active component. For this example, it is assumed that at unit concentration the spectrally active component (which is the analyte of interest) exhibits the Gaussian absorbance spectrum illustrated in FIG. 1 with q=101 frequencies. Following Beer's Law for a single component system, when the concentration of the analyte of interest is x, the i$^{th}$ element (t=1, 2, ..., q) of the spectrum is $$y_t = x \cdot b_t + \epsilon_t, \quad \text{[Equation 2]}$$

where $$b_t = \frac{1}{\sqrt{2\pi}} \cdot \exp\{-.5 \cdot (-8 + .16 \cdot (t-1))^2\}$$

and the $\epsilon_t$ are independent and identically distributed normal ($\mu=0$, $\sigma^2=0.01$) measurement errors. Note that frequency 51 (t=51) has the largest signal and therefore the best signal-to-noise characteristics. In contrast, frequencies far away from the center of the frequency range contain virtually no signal and therefore have very poor signal-to-noise characteristics.

A small simulation study was conducted to evaluate the effect on the predictive ability of three full-spectrum calibration methods in conjunction with various subsets of the spectrum. The three full-spectrum methods are PLS, and two variations of a method based on the explicit Beer's Law model (Eqn. 2). PLS modeling was performed by using one latent variable and centering both concentration and spectral data. The two variations of the method based on the explicit model (denoted LS/LS and LS/ML) are differentiated by the methods used in the prediction phase. The model parameters, $\{b_t\}$, are estimated similarly in the calibration phase for both variants of the method using least-squares regression and the explicit model given by Eqn. 2. Estimation of the analyte concentration of a new sample $\chi$ by using $\{\hat{b}_t\}$ and its associated new spectrum (Y) is accomplished by using least-squares regression (LS/LS) and maximum likelihood estimation (LS/ML). Note that of the three calibration methods that were considered, only PLS is suitable for use in complex situations with unknown spectrally active components with overlapping spectral features. Six different subsets of the 101 frequencies were used for analysis. They are $A_1=\{49, 50, 51, 52, 53\}$, $A_2=\{46, 47, \ldots, 56\}$, $A_3=\{41, 42, \ldots, 61\}$, $A_4=\{31, 32, \ldots, 71\}$, $A_5=\{21, 22, \ldots, 81\}$, and $A_6=\{1, 2, \ldots, 101\}$. Note that the frequency subsets are centered around frequency 51 and add increasing numbers of additional frequencies. $A_1$ contains the five frequencies with the best signal-to-noise, while $A_6$ contains all 101 frequencies, many of which contain very little useful signal.

For the simulation study fifty calibration sets were generated, each with five observations. The set of analyte concentrations corresponding to the five observations are $\{0.1, 0.3, 0.4, 0.5, 0.7\}$. For each observation, a spectrum was constructed based on Eqn. 2. Calibration models using each of the six sets of frequencies ($A_1, A_2, \ldots, A_6$) were constructed using PLS and least-squares regression. For each calibration set, fifty new spectra were generated based on Eqn. 2 with a fixed analyte concentration, $\chi$. These spectra along with the constructed calibration models and prediction methods were then used to predict $\chi$. This complete procedure was repeated three times with $\chi \in \{0.1, 0.5, 0.9\}$ The root mean squared error of prediction, $$RMSEP = \sqrt{\frac{1}{50} \cdot \sum_{i=1}^{50} (\hat{\chi}_i - \chi)^2} ,$$

where $\hat{\chi}_i$ the predicted value of $\chi$, for each of the various simulation conditions (defined by $\chi$, the calibration method, and frequency set) is set forth in Table 1.

TABLE I

| | | RMSPE versus Frequency Subset | | | | | |
| | | Frequency Subset | | | | | |
| $\chi$ | Method | $A^1$ | $A^2$ | $A^3$ | $A^4$ | $A^5$ | $A^6$ |
|---|---|---|---|---|---|---|---|
| .1 | PLS | .145 | .118 | .140 | .176 | .196 | .235 |
| | LS/LS | .114 | .084 | .073 | .070 | .069 | .070 |
| | LS/ML | .121 | .090 | .081 | .083 | .087 | .099 |
| .5 | PLS | .110 | .087 | .079 | .081 | .081 | .088 |
| | LS/LS | .131 | .100 | .097 | .119 | .144 | .189 |
| | LS/ML | .140 | .109 | .091 | .092 | .094 | .107 |
| .9 | PLS | .179 | .193 | .203 | .268 | .321 | .375 |
| | LS/LS | .150 | .134 | .126 | .190 | .234 | .338 |
| | LS/ML | .163 | .128 | .109 | .107 | .107 | .117 |

From Table 1, it is apparent that the effect of including frequencies that have poor S/N depends on both the calibration method and the value of $\chi$. The ability to predict $\chi$, provided by LS/ML appears to be rather insensitive to the inclusion of irrelevant frequencies for all three values of $\chi$. On the other hand, the prediction abilities of PLS and LS/LS are quite sensitive to the inclusion of irrelevant frequencies for two of the three values of $\chi$. Except in the instance where $\chi=0.5$, the performance of PLS degenerates significantly as more and more frequencies with poor S/N are included. PLS performance is insensitive to the inclusion of irrelevant frequencies when $\chi=0.5$. This is due to the fact that, with a poor model, PLS-predictions tend to be biased toward the average value in the calibration set, which in this case is close to 0.5. Except in the case where $\chi=0.1$, the performance of LS/LS degenerates significantly as more and more frequencies with poor S/N are included. The performance of LS/LS is insensitive to using irrelevant frequencies when $\chi=0.1$ because of the fact that use of LS in the prediction phase tends to produce predictions biased towards zero, which is relatively close to 0.1 (see Thomas 1991). From this simple study it is clear that use of irrelevant frequencies can seriously degrade the performance of full-spectrum calibration methods. Note that other full-spectrum methods, such as PCR, also exhibit behavior wherein if irrelevant wavelengths are included, predictions tend to be biased towards the average value of the analyte of interest in the calibration set.

As described above, PLS becomes increasingly sensitive to the inclusion of additional wavelengths when utilizing the algorithm to predict on analyte concentrations removed from the average. This fact of PLS analysis is extremely relevant in designing a noninvasive glucose monitor. In patients with and without diabetes the average glucose concentrations are approximately 150 and 100 mg/dL, respectively. Due to an inability to control their glucose levels, diabetic patients' glucose level can fall below 80 mg/dl. At this point the patient starts to become hypoglycemic. Hypoglycemia, especially below 50 mg/dl, is a very dangerous condition as the patient can experience "insulin shock" and become comatose. Diabetic patients fear hypoglycemia because they no longer function normally and are often unaware of the compromised state.

If all wavelengths are included, PLS predictions will tend to be biased toward the average value of glucose in the calibration set. In operation a patient may have a glucose concentration of 80 mg/dl but a monitor using all wavelengths might predict 100 mg/dl. Given this information, a diabetic patient may take no action to correct his/her glucose level, even though approaching a dangerously low level. If no action is undertaken, the patient may experience severe hypoglycemia and its possibly severe consequences. Thus, accurate readings at below average glucose concentrations are extremely important. The ability to select those wavelength subsets for use in the multivariate algorithm that maximize performance and minimize PLS' tendency to bias extreme results to the average is of importance in the design of a noninvasive home glucose monitor for use by the diabetic patient.

Despite the importance of wavelength selection as demonstrated above, effective methods for wavelength selection remain inadequate for complex situations requiring multivariate spectral analysis. This is especially true when Beer's law is not followed or when not all components are known. In conditions where Beer's Law is followed and all spectrally active components in the sample material (and associated spectra) are known, then except for measurement error, the q-vector of absorbancies for a single sample ($y_i$) is given by $y_i = B \cdot x_i$, where $x_i$ is the p-vector of concentrations, and $B=(b_1, b_2, \ldots, b_p)$ contains the spectra of each of the p spectrally active components when each are at unit concentration. If B is known, there are various approaches for selecting wavelengths (see e.g., Kalivas, J. H., and Kalivas, J. H., "Evaluation of Experimental Designs for Multicomponent Determinations by Spectrophotometry," *Analytica Chimica Acta*, 207, 125–135 (1988)). These approaches are most often used in conjunction with inverse least-squares regression (see Haaland, D. M., and Thomas, E. V., "Partial Least-Squares Methods for Spectral Analyses. 1. Relation to Other Quantitative Calibration Methods and the Extraction of Qualitative Information," *Analytical Chemistry*, 60, 1193–1202 (1988)) and related procedures where it is possible to use only a limited number of spectral wavelengths. For example, suppose that $\mathscr{F}$ is a subset of the q potential wavelengths containing $q^*$ elements. Let $B\mathscr{F}$ represent the corresponding $q^* \times p$ submatrix of B. Procedures have been proposed for searching for subsets of wavelengths that optimize some metric relating to sensitivity and/or selectivity of the frequency set to the analyte of interest, such as the condition number of $B\mathcal{F}$ (see e.g., Juhl and Kalivas 1988). For example, Kalivas, J. H., Roberts, N., and Sutter, J. M., "Global Optimization by Simulated Annealing with Wavelength Selection for Ultraviolet-Visible Spectrophotometry," *Analytical Chemistry*, 61, 2024–2030 (1989), advocate using simulated annealing and Lucasius, C. B., and Kateman, G., "Genetic Algorithms for Large-Scale Optimization in Chemometrics: An Application," *Trends in Analytical Chemistry*, 10, 254–261 (1991) propose using genetic algorithms to search for wavelengths that minimize the condition number of $B\mathcal{F}$. All of these procedures assume that Beer's Law is followed and the spectra of all spectrally active components in the sample material are known. Unless Beer's Law is followed, the optimization metrics associated with these procedures do not necessarily relate directly to prediction performance. Thus, the usefulness of these methods in complex situations is limited.

Li, Tong-Hua, Lucasius, C. B., and Kateman, G., "Optimization of calibration data with the dynamic genetic algorithm," *Analytica Chimica Acta*, 268, 123–234 (1992) describe the use of genetic algorithms (GAs) to "optimize calibration data sets and enhance the predictive ability of a calibration model successfully". Additionally, Li, et al. state that "GAs should be tested on higher level problems." In summary, the article by Li, et al., teaches the use of genetic algorithms for wavelength selection utilizing the predicted error sum of squares (PRESS) as the fitness function. However, the article does not teach how to interpret the resulting data nor how to perform the wavelength selection process for development of optical instruments. No mention is made of minimizing instrument cost or how to specifically optimize instrument performance. Further, no mechanism or method is described for selection of those wavelengths or wavelength subsets that yield optimal results. Thus, the article is a general overview of genetic algorithms but does not teach a method or methodology for implementation in a practical, systematic manner. In addition to the foregoing, as Li, et al. was published in October 1992, applicants do not concede that it is prior art to them.

In complex situations, where Beer's Law does not provide a good approximation throughout the spectrum or not all spectrally active components are known, there are very few existing procedures for wavelength selection. Most procedures are associated with calibration methods (e.g., inverse least squares) that are capable of using relatively few wavelengths because of problems with collinearity of the spectral measurements. Stepwise (forward) regression is often used in conjunction with these calibration methods (e.g., see Hruschka (1987)). Although this procedure can utilize the synergy among wavelengths, it is often fraught with difficulties such as overfitting.

In the process of performing quantitative spectroscopy, there are two important terms to understand clearly. Those wavelengths that are "predictive" are those wavelengths that are useful in modeling the relationship between spectral information and analyte concentration. "Synergistic" wavelengths are those wavelengths that when used singularly have a given ability to model the relationship between spectral information and analyte concentration, but when used together have an enhanced capability of modeling the relationship.

Other procedures search for wavelengths which empirically exhibit good selectivity, sensitivity, and linearity for the analyte of interest over the training set. Consider the model $y_{it} = a_t + x_i \cdot b_t + f_{it} + \epsilon_{it}$ where $x_i$ is the analyte concentration of the $i^{th}$ sample in the calibration set, $y_{it}$ is the response of $i^{th}$ sample at the $t^{th}$ wavelength, $a_t$ and $b_t$ are parameters, $f_{it}$ represents contributions from other spectrally active components and/or deviations from Beer's Law due the presence of nonlinearities, and $\epsilon_{it}$ is a random measurement error with a mean of zero and variance, $\sigma_t^2$. The object of these search procedures is to find wavelengths where $b_t$ is relatively large for a single analyte and $f_{it}$ and $\epsilon_{it}$ are relatively small for all samples in the training set. In conjunction with full-spectrum and limited-wavelength calibration methods, near-infrared spectroscopists often rely on correlation plots (e.g., see Hruschka 1987) to search for appropriate wavelengths for use. Based on the n samples in the calibration set, a correlation plot is a spectrum given by the set of univariate correlations, $\{R_t\}$, between the $x_i$'s and $y_{it}$'s. Wavelengths whose measurements exhibit a high degree of correlation with the amount/concentration, of the analyte of interest, measured by $R_t^2$, are selected. This technique does not account for synergy among the different wavelengths.

A related method was recently proposed by Brown et al. (1991) and Brown (1992). Rather than use $R_t^2$ as a measure for selecting wavelengths, Brown and his colleagues recommend selecting wavelengths associated with large values of $$\frac{\hat{b}_t^2}{\hat{\sigma}_t^2},$$

where $\hat{b}_t$ is the simple least-squares estimate of $b_t$ and $\hat{\sigma}_t^2$ is an estimate of $\sigma_t^2$. Again, this method does not account for synergy among measurements at different wavelengths. As set forth in the Description of the Preferred Embodiment, this synergy can be very desirable.

In order for the correlation plot or the method proposed by Brown and his colleagues to be useful, wavelengths specific to the analyte of interest with good signal-to-noise are needed. However, the required wavelength specificity is not always available. For example, in the near-infrared spectrum there is considerable overlap between spectral responses of many different chemical species which often appear together in biological specimens. Therefore, it is very doubtful whether these have much utility when analyzing complex biological materials, such as human tissue in this or any other spectral region.

Because subject-matter knowledge is insufficient to select wavelengths and the search space of possible wavelength subsets is too large to be searched exhaustively ($2^q$ possible combinations of wavelength subsets, where q can be in the hundreds or thousands), some method is needed to determine which points in the search space should be sampled. We have determined that the use of genetic selection criteria, specifically genetic algorithms, form a class of techniques for carrying out this search. Genetic algorithms rely on the analogy between a bit string and a chromosome. Under this analogy, an initial population of bit strings (subsets of wavelengths) is generated randomly. The fitness of each member of the population is evaluated. The fitness values are used to eliminate weak individuals (subsets with low fitness) and replicate those with high fitness. Through interation of this procedure, the genetic algorithm will eventually converge to wavelength subsets that have high fitness (meaning low cost/high performance).

The seminal work on genetic algorithms was provided by Holland, J. H., "Genetic Algorithms and the Optimal Allocations of Trials," *SIAM Journal of Computing*, 2, 88–105 (1973), and *Adaptation in Natural and Artificial Systems*, The Univeristy of Michigan Press: Ann Arbor (1975). Since then, there has been a great deal of activity in the area. Unlike traditional methods of optimization, genetic algorithms have been shown to work well over a broad range of difficult problems (e.g., see Davis, L. (editor), *Handbook of Genetic Algorithms*, Van Nostrand Reinhold (1991). Goldberg, D. E., *Genetic Algorithms in Search, Optimization, and Machine Learning*, Addison-Wesley (1989) provides a very readable introduction to genetic algorithms as well as applications which include problems in science, business, and engineering. In the area of chemometrics several authors have very recently proposed using genetic algorithms in a number of applications (see e.g. Li, et al. (1992), and Lucasius, et al., (1991)).

With regard to the use of genetic algorithms in the context of wavelength selection, first, suppose that there are q potential wavelengths to choose from when building a calibration model. The notion of a binary string, S, with dimension q, will be used to indicate the set of wavelengths that are used to build the model. This binary representation is key to using genetic algorithms for this problem. The biological analog of S is a chromosome. Each binary element of S, analogous to a gene, indicates whether its associated wavelength is or is not used for modeling. For example, if S=$\{1, 1, 0, 1, 0, 0\}$, then wavelengths 1, 2, and 4 (of six) are used for modeling. With the additional specification of the method used to build the calibration model (e.g. PLS), S provides a straightforward index for model identification.

In order to search for sets of wavelengths (represented by binary strings) that yield good performance, it is necessary to specify a reasonable performance metric, denoted here by the term fitness (F). The fitness of a certain wavelength subset (represented by a binary string) is a single numerical measure of how well that subset meets these criteria. The likelihood that an individual binary string contributes to the next generation of binary strings is related directly to the fitness of that string. In the analogous context of Darwinian evolution, the likelihood that an individual will live (hence contribute genetic material to the next generation) is related directly to the fitness of that individual. For wavelength selection purposes, we will allow the fitness of each string to be various decreasing functions of the standard error of prediction (SEP) based on cross validation (see Stone, M., "Cross-Validatory Choice and Assessment of Statistical Predictions," *Journal of the Royal Statistical Socieity, Series B*, 36, 111–133 (1974)). Also note that, unlike the metric proposed by Lucasius and Kateman, 1991 (condition number), the SEP is a direct measure of performance. The SEP is, however, a very complicated non-linear function of S and can be obtained only through intensive computational means.

The inadequacies of the prior methods can be overcome by the use of a systematic search or optimization process based on genetic algorithms. Genetic algorithms differ from traditional methods of optimization in some important ways. While most traditional methods of optimization move from a single point in the search space to another, genetic algorithms move from a set of points to another set. Each successive set of points will be referred to as a generation, with each generation containing r binary strings. Unlike traditional methods of optimization that rely on deterministic transition rules to move throughout the search space, genetic algorithms use probabilistic transition rules embodied within a number of operators. The three operators that are common among the many variations of genetic algorithms are reproduction, crossover, and mutation.

The first step is to form the first generation of the S's, consisting of r q-dimensional binary strings and denoted by $G^1 = \{S_1^1, S_2^1, \ldots, S_r^1\}$. Note that the effectiveness of the genetic algorithms depends on the diversity within $G^1$. Therefore, pseudo-random number generators are often used to create this first generation of strings. Next, the fitness of each of the models specified by the r strings in $G^1$ are obtained.

The next generation of bit strings, $G^2 = \{S_1^2, S_2^2, \ldots, S_r^2\}$, is formed in three stages. First, r individual strings are selected from $G^1$ with replacement, where the probability of selecting an individual string is proportional to its fitness. This process is referred to as reproduction. The reproduced strings are used as the basis for constructing the next generation. In this way, strings with a higher fitness values will have a higher probability of contributing to the next generation. Following reproduction, crossover proceeds in two steps. First, members of the newly reproduced strings are paired (mated) at random. Second, each pair of mated strings undergoes crossing over as follows: an integer position k along the string is selected at random between 1 and q-1. Two new strings are created by swapping all bits between positions k+1 and q inclusively. Finally, mutation (bit flipping) is employed with low probability across all bits of the newly reproduced strings modified by crossover. Mutation plays a dual role in the search procedure by providing and maintaining diversity in the population of binary strings while working as a search operator in its own right. The following example illustrate the procedure.

Assume that the number of possible wavelengths is six (q=6), the generation size is four (r=4), and the fitness for each of the strings in the first generation is as indicated in Table 2 below.

TABLE 2

| String ID | String | Fitness |
|---|---|---|
| $S_1^1$ | 011010 | 1 |
| $S_2^1$ | 110001 | 4 |
| $S_3^1$ | 010001 | 3 |
| $S_4^1$ | 100110 | 2 |

Suppose that reproduction yields the intermediate strings $S_1^{1+}$=110001, $S_2^{1+}$=010001, $S_3^{1+}$=100110, and $S_4^{1+}$=110001. In this instance, the string in $G^1$ with the highest fitness ($S_2^1$) was copied twice while that with the lowest fitness ($S_1^1$) was not copied at all. Now suppose that the intermediate strings $S_1^{1+}$ and $S_2^{1+}$ are paired for crossover ($S_3^{1+}$ and $S_4^{1+}$ are also paired). Also suppose that the crossover sites (k) are randomly selected to be 4 and 2. Except for mutation, formation of the second generation is completed as indicated in Table 3. That is, the last two bits of $S_1^{1+}$ are swapped with the last two bits of $S_2^{1+}$ and the last four bits of $S_3^{1+}$ are swapped with the last four bits of $S_4^{1+}$.

TABLE 3

| | Formation of Generation | | |
|---|---|---|---|
| j | String ($S_j^{1+}$) | Crossover Site | String ($S_j^{2+}$) |
| 1 | 110001 | 4 | 110001 |
| 2 | 010001 | 4 | 010001 |
| 3 | 100110 | 2 | 100001 |
| 4 | 110001 | 2 | 110110 |

This evolutionary optimization proceeds from one generation to the next by using the fitness values associated with the strings in $G^i$ to help select $G^{i+1}$. The evolutionary process is terminated at some predetermined point or when the "genetic fitness" of new generations fails to improve significantly. The overall procedure is summarized in algorithmic form below.

INIT: Initialize Random Number Generator (RNG);

$i \leftarrow 0$;

NEXTGEN: Repeat until (Fitness ceases to improve or $i = i_{max}$);

$i \leftarrow i + 1$;

If ($i = 1$);

Form $G^i = \{S_1^i, S_2^i, \ldots, S_r^i\}$ using RNG;

Else;

Form $G^i = \{S_1^i, S_2^i, \ldots, S_r^i\}$ using $G^{i-1}$, $\{F(S_1^{i-1}), F(S_2^{i-1}), \ldots, F(S_r^{i-1})\}$, and reproduction, crossover, and mutation;

End;

$j \leftarrow 0$;

NEXTSET: Repeat Until ($j$ = generation size ($r$));

$j \leftarrow j + 1$;

$k \leftarrow 0$;

CVALID: Repeat Until ($k$ = number of samples ($n$));

$k \leftarrow k + 1$;

Construct model without $k^{th}$ sample: $M(S_j^i, -k)$;

Predict $x_k$ using $M(S_j^i, -k)$: $\hat{x}_k$;

End;

$$SEP(S_j^i) = \sqrt{\frac{1}{n} \sum_{k=1}^{n} (\hat{x}_k - x_k)^2} \;;$$

$F(S_j^i) \propto \{SEP(S_j^i)\}^{-h}$, with $h > 0$;

End;

End;

There are a number of interesting and important issues associated with implementing genetic algorithms for wavelength selection for the applications disclosed and claimed herein. One important need is to reliably select wavelengths. That is, the ideal procedure should minimize the inclusion of irrelevant (or difficult) wavelengths without omitting useful wavelengths. The nature of typical spectral problems (few calibrating spectra with many wavelengths) tends to make this a very difficult problem. Other important issues are associated with making the procedure computationally tractable in a reasonable period of time. The inherent parallel nature of genetic algorithms and cross-validation, combined with massive computing requirements, make this method well suited to take advantage of massively parallel computing.

Genetic algorithms form a very flexible family of procedures that provides the user with some ability to tailor the search procedure for a particular problem. This flexibility is manifested in a number of user selectable options such as the form of the fitness function (F), the probability of mutation ($p_m$), the generation size ($r$), and the mechanism used to produce the first generation.

For wavelength selection, a reasonable candidate family for the fitness function is F=f (performance, cost). Some issues that define the performance are: a measure of the size of calibration residuals (e.g., SEP), the ability of the selected wavelength subsets to identify outliers, and the range of values of the analyte of interest that can be reliably predicted by the model. Cost issues are general in the sense that they involve both the manufacturability and operation of the instrument. For example, there is a certain manufacturing cost associated with obtaining each spectral feature. This cost may depend on the wavelength location, range of the individual feature, and spectrometer resolution. Operational costs may involve such issues as the time required to obtain the spectral measurements.

For the foregoing fitness function, consider specific variations of F's such that F $\alpha$ $SEP^{-H}$, with $H \geq 1$. Generally, the convergence rate of the genetic algorithms increases as H increases. However, if the convergence rate is too rapid, the genetic algorithms may not sample enough of the search space; the result being suboptimal. Users of genetic algorithms commonly select values for $p_m$ in the range from 0.001 to 0.01 (e.g, see Goldberg). In general, by increasing $p_m$, the distribution of F (within a generation) tends to spread out and the convergence rate is slowed. Conversely, by decreasing $p_m$, the convergence rate is increased with an increased risk of convergence to local optima. Typically, users of genetic algorithms select values for r in the range from 50 to 200 (e.g., see Goldberg (1989)). In general, the likelihood of converging to near-optimal wavelength sets improves as r increases due to the increased pool of "genetic material." Increased computational expense is the penalty for increasing r. It is usually important to make the initial binary strings within $G^1$ diverse. However, in some situations, one may deliberately introduce structure into $G^1$. For instance, suppose certain wavelengths are a priori known to be important (e.g., if isolated spectral features of the analyte are available, the wavelengths corresponding to the isolated features should be selected). In these cases, the bits associated with these wavelengths can be set to one for all sets within $G^1$ and succeeding generations.

Since genetic algorithms can be used in combination with a variety of calibration methods (e.g., PLS, PLS2, PCR and neural networks), it is also necessary to specify the method before beginning the wavelength search. Furthermore, use of methods like PLS and PCR involve determining the appropriate model size (e.g., number of latent variables/factors involved). There are various ways to approach this problem. One simple way is to do a preliminary analysis to establish the appropriate model size when using all wavelengths $h_{all}$, and to use this single model size throughout the iterations of the genetic algorithms. When using this procedure, relatively good sets of wavelengths (given $h_{all}$) will be obtained. Note, however, that a better choice of model size/wavelength set may be obtained if the genetic algorithms iterations involve variable model sizes. This can be accomplished by expanding the binary string, S, with bits that represent the model size. One would choose $h_{max}$ as an upper bound on the model size. The number of additional bits required is $b = \lceil \log_2(h_{max}-1) \rceil$, so that the total number of bits in the binary string is $q^+ = q+b$. Alternatively, the genetic algorithm could be applied to all sizes of model up to $h_{max}$ with the wavelength subsets model resulting in the best fitness being chosen as the optimal model.

As described above the binary string can be expanded to include both the wavelength information and model size. The information content of the binary string can be further expanded to include any variable that might improve the fitness of the determination. In the area of noninvasive medical instrumentation such parameters may include a variety of physiological and physical measurements. For example, inclusion of finger thickness in the binary string could improve the fitness determination. Possible variables to be considered include melanin content (i.e., ethnicity), finger temperature, finger diameter, patient gender, patient age, pressure on finger, or information on blood chemistries.

In addition to optimizing performance of the multivariate algorithm and model, the genetic selection process can be utilized to minimize instrument cost. Currently the cost of an instrument is minimized by having the engineering group involved attempt to utilize the least expensive components available that enable the instrument to perform adequately. Such a process is reasonable when considering simplistic instrument designs but unreasonable when developing complex medical instrumentation. It is virtually impossible for a given individual to simultaneously understand the relationship between instrument performance specifications, their cost relationship, and their influence on the overall performance of the instrument. Through the genetic selection process and incorporation of these cost/performance parameters in the fitness function, both performance and cost can be optimized concurrently.

End product instrument cost is defined by numerous parameters but the three major cost considerations are: (1) spectral region used; (2) number of wavelengths measured; and (3) spectral resolution requirements of the instrument. Depending upon the type of instrumentation used, these cost parameters are incorporated in the fitness function differently. In fact, the cost ramifications of any given instrument configuration can be included in the fitness function. The additional cost parameters could include the time needed to take the measurement and the ease of manufacturability. Several examples will illustrate the complexity of improving performance while minimizing instrument cost.

We have recently demonstrated the ability to measure alcohol noninvasively using infrared spectroscopy consistent with the technology set forth in U.S. Pat. No. 4,975,581. The characteristics of alcohol measurement suggest that a commercial instrument might involve the use of a filter instrument. The major cost variables associated with a filter instrument are number of filters used and the resolution requirements of the optical filters. For alcohol, the wavelength region used can be quite broad and is not a major cost driver. Thus, in simplistic terms the fitness function might look like:

Fitness=$f$ {(performance), (2 * wavelength region), (9 * number of filters), (8 * spectral resolution)} where weights between 1 and 10 are applied to the three listed cost parameters.

In addition to noninvasive alcohol monitoring, we have performed extensive research in the area of noninvasive glucose monitoring. See: (1) "Post-Prandial Blood Glucose Determination by Quantitative Mid-Infrared Spectroscopy", K. J. Ward, D. M. Haaland, M. R. Robinson and R. P. Eaton, *Applied Spectroscopy*, Vol. 46, No. 6, 1992, pages 959–965, (2) "Reagentless Near-Infrared Determination of Glucose In Whole Blood Using Multivariate Calibration", D. M. Haaland, M. R. Robinson, G. W. Koepp, E. V. Thomas, and R. P. Eaton, *Applied Spectroscopy*, Vol. 46, No. 10, 1992, pages 1575–1578, and (3) "Noninvasive Glucose Monitoring in Diabetic Patients: a Preliminary Evaluation", M. R. Robinson, R. P. Eaton, D. M. Haaland, G. W. Koepp, E. V. Thomas, B. R. Stallard and P. L. Robinson, *Clinical Chemistry*, Vol. 38, No. 9, 1992, pages 1618–1622. The work to date indicates that accurate glucose measurement will require the use of more wavelengths than is required for alcohol. Thus, a possible commercial monitor may utilize acousto-optic tunable filters (AOTF). AOTFs are solid-state devices which utilize acousto-optic interactions in an anisotropic medium. The interaction process leads to a change in wavelength and in direction of the incident beam. The resulting diffraction process has been successfully exploited in AOTFs. The result is a compact solid-state spectrometer that can be tuned electronically in a matter of microseconds over a wide spectral range encompassing both the UV and IR regions. Due to its solid-state design, there are no moving parts. AOTFs have variable resolution depending upon crystal size. See "Acousto-optic devices", Chieu D. Tran, *Analytical Chemistry*, Vol 64, No. 20, Oct. 15, 1992). Also see; Photonics Global Forecast, Defense-Related Acousto-Optics Transform Commercial Products, R. G. Rosemeier, Photonics Spectra, 83–84, January, 1993; U.S. Pat. No. 4,883,963 to G. J. Kemeny et al.; and U.S. Pat. No. 5,120, 961 to K. H. Levin et al. The cost parameters associated with AOTF are quite different than a filter instrument. Specifically, except for increased measurement time, there is no additional cost associated with measuring multiple wavelengths. In contrast to filters, AOTFs are limited to operating over approximately a 1000 nm region. Use of this technology over a wider range would be extremely expensive. The resolution of the AOTF can be increased through the use of longer crystals which translates to additional expense. Thus, the fitness function for the three parameters given the cost consequences of AOTF might be as follows:

Fitness=$f$ {(performance), (10 * wavelength region), (1 * number of wavelengthss), (5 * spectral resolution)}

In addition to blood chemistry analysis, work has been done on the development of a fetal oximeter. Although there are significant differences in the measurement criteria associated with the noninvasive fetal oxygen saturation when compared with noninvasive blood analysis, genetic selection can also be used in the development process of such an instrument. In the case of fetal oximetry the vast majority of the information exists in the 500 to 1000 nm region. This wavelength region can be recorded using linear silicon array detectors which are commercially available and inexpensive. Thus, the use of a fixed grating spectrometer is reasonable. With a fixed grating spectrometers the wavelength region, resolution and number of wavelengths recorded are all closely related. The number of array diodes on the detector, the size of the diodes, groove density of the grating, and the entrance slit are important design parameters. These parameters define wavelength region, number of wavelengths, and spectral resolution. Thus, the cost parameters associated with this system are different than the preceding filter or AOTF instruments. An appropriate fitness function might take the following form:

Fitness=$f$ {(performance), (5 * wavelength region), (5 * number of wavelengths), (5 * spectral resolution)}

In addition to the preceding, significant work has been performed in the development of a noninvasive arterial blood gas monitor. This device enables the simultaneous measurement of all five blood gas parameters (i.e., pH, [$HCO_3^-$], $PCO_2$, $PO_2$, and $O_2$ saturation). Our prior investigations indicate that the measurement can be made using a discrete set of diodes. The commercial monitor may thus include a set of wavelength specific diodes and a single detector. The expense of diodes will vary depending upon the wavelength region. Diodes in the 500–1000 nm region are readily available and quite inexpensive. At longer wavelengths the diodes become more expensive. In this condition the cost portion of the fitness function will be variable to account for these differences. The number of wavelengths measured is tied to the number of diodes used. Thus, each additional wavelength results in an incremental cost. As some diodes emit wavelengths in a narrow band pass, the cost associated with high resolution is not enormous. With the various characteristics of diode instruments accounted for the fitness function could be defined as follows:

Fitness=$f$ {(performance), ((variable weighting) * wavelength region), (9 * number of wavelengths), (2 * spectral resolution)}

Through incorporation of both performance and cost in the fitness function, these two parameters can be optimized through the use of genetic selection criteria.

It is an object of the present invention to design quantitative spectroscopic instrumentation with the best possible performance achieved through wavelength selection. Specifically, the use of genetic selection criteria optimizes the performance of noninvasive medical instrumentation.

It is another object of the invention to design quantitative spectroscopic instrumentation for minimal cost. Specifically, the use of genetic selection criteria minimizes the cost of noninvasive medical instrumentation.

SUMMARY OF THE INVENTION

In a method for determining one or more unknown values of at least one known characteristic, such as the concentration of an analyte in a biological material (e.g. glucose, alcohol, blood urea nitrogen (BUN), bilirubin, hemoglobin, creatine, electrolytes, ketones, fatty acids, lipoproteins, triglycerides, white blood cells, hematocrit, and cholesterol), with a model based on a set of samples with known values of the characteristic and an algorithm capable of using more wavelengths than samples in the set of samples, such as disclosed and claimed in the U.S. Pat. No. 4,975,581, the improvement comprising selecting multiple wavelength subsets, from the electromagnetic spectral region appropriate for determining the known characteristic, for development of an improved model. The algorithm with the improved model increases the fitness for the determination of the unknown values of the known characteristic. The subset selection process utilizes multivariate search methods that select both predictive and synergistic wavelength subsets within the range of wavelengths utilized to irradiate the sample set with known charactistic values. Each of the subsets includes at least one wavelength. The subset selection step is made independent of the knowledge of the spectral features of the characteristics of the biological material other than the knowledge of the known characteristic. Further, the fitness of the determination (F) is defined as F=f (cost, performance), wherein factors such as measurement time, instrument resolution, wavelength range, and the number of wavelength subsets measured can be utilized in determining the "cost" contribution to fitness. Similarly, factors such as standard error of prediction (SEP), outlier detection, the range of values of the known characteristic covered by the model, the robustness of the model, and the ease of transferability of said model can be utilized in determining said "performance" contribution to the fitness. Preferably, the wavelength subset selection process utilizes a genetic algorithm.

In addition to the foregoing, the method includes the steps of: (1) using one or more applications of the genetic algorithm to produce one or more count spectra, with multiple count spectrum then combined to produce a combined count spectrum; (2) smoothing the count spectrum; (3) selecting a threshold count from a count spectrum to select these wavelength subsets which optimize the fitness function; and (4) eliminating a portion of the selected wavelength subsets.

Preferably the algorithm is a full spectrum algorithm selected from the group including PLS, PLS2, PCR, CLS, Q-matrix, cross-correlation, Kalman filtering, neural networks, and continuum regression. The determination of the unknown values can be made: (1) noninvasively and in vivo; (2) invasively and in vivo; or (3) in vitro.

The foregoing can also be utilized for: (1) improving the determination of blood gas parameters (i.e., pH, [$HCO_3^-$], $PCO_2$, $PO_2$, and $O_2$ sat.) in a biological material (particularly in a human), as disclosed and claimed in pending U.S. patent application Ser. No. 07/910,004; and (2) improving the determination of the blood oxygen level in a mammal, as disclosed and claimed in pending U.S. patent application Ser. No. 07/729,452.

Finally, the invention includes apparatus based on the foregoing improvement.

U.S. Pat. No. 4,975,581 and pending application Ser. Nos. 07/729,452 and 07/910,004, all of which are commonly owned, and are incorporated by reference.

BRIEF DESCRIPTION OF THE DRAWINGS

FIGS. 2A–2I illustrates distribution of the SEP versus generation for each genetic algorithm using the three synthetic data sets (A, B, and C), wherein summary percentiles are represented by * (minimum and maximum), ---- (1st and 3rd quartiles), and ——— (median), and wherein for comparison, the SEPs when all 100 wavelengths are used and when only the 10 relevant wavelengths are used, are indicated by parallel solid lines;

DESCRIPTION OF THE PREFERRED EMBODIMENTS

In order to illustrate the use of genetic algorithms for wavelength selection and to present additional implementation guidelines, consider the following artificial example with the following simple structure. Suppose, $$y_{it} = x_i + \delta_i + \epsilon_{it}, \quad t = 1, 2, \ldots, 5 \quad \text{[Equation 6]}$$
$$= 67_i + \epsilon_{it}, \quad t = 6, 7, \ldots, 10$$
$$= 2 \cdot \epsilon_{it}, \quad t = 11, 12, \ldots, 100, \text{where}$$

$y_{it}$ is the response of the $i^{th}$ sample at the $t^{th}$ measured wavelength, $x_i$ is the analyte concentration of the $i^{th}$ sample, $\delta_i$ and $\epsilon_{it}$ are independent random normal errors with mean zero and variances $\sigma_\delta^2=1.0$ and $\sigma_\epsilon^2=0.0025$, respectively.

In a spectroscopic context, we could conceive of $\epsilon_{it}$ (or $2 \cdot \epsilon_{it}$) as the basic measurement noise and $\delta_i$ as a relatively large contribution to the $i^{th}$ spectrum due to a interfering species randomly varying in concentration. Note that the analyte of interest directly influences only the first five wavelengths. Wavelengths 6–10, while not directly influenced by this analyte, can be useful when constructing a calibration model, by correcting the measurements at the first five responses for the effects of $\delta_i$. Thus, it is important to capture the synergy between wavelengths 1–5 and wavelengths 6–10.

Note that existing approaches for wavelength selection that consider wavelengths individually, such as the correlation plot, will not select wavelengths 6–10. Finally note that wavelengths 11–100 are irrelevant and have a relatively high level of measurement noise. Thus, use of these wavelengths adversely affects the resulting calibration model.

Three realizations of a synthetic data set (A, B, and C), based on Equation 6 were generated. Each data set consisted of ten calibration samples (i.e., n=10), with analyte concentrations {0.1, 0.2, . . . , 1.0}, and associated simulated responses. Each data set was submitted three times to a genetic algorithm with the following attributes: r=50, $p_m$=0.005, and F=SEP$^{-4}$. For illustrative purposes, this fitness function involves only one aspect of performance (i.e., SEP) and does not include cost. Each time a data set was submitted to the genetic algorithm, a unique initial generation (G$^1$) was constructed by randomly assigning 1's (with probability 0.5) to each bit of each of the 50 binary strings of G$^1$. The SEP was obtained by n-fold cross-validation (one sample out-at-a-time) of a two-factor PLS model. Here, note that two factors are optimal because there are two structural sources of variation in Equation 6. IMSL© routines RNNOR and RNUN were used to generate pseudo-random numbers for construction of the synthetic data sets as well as for use by the probabalistic operators of the genetic algorithm.

Figure 1:
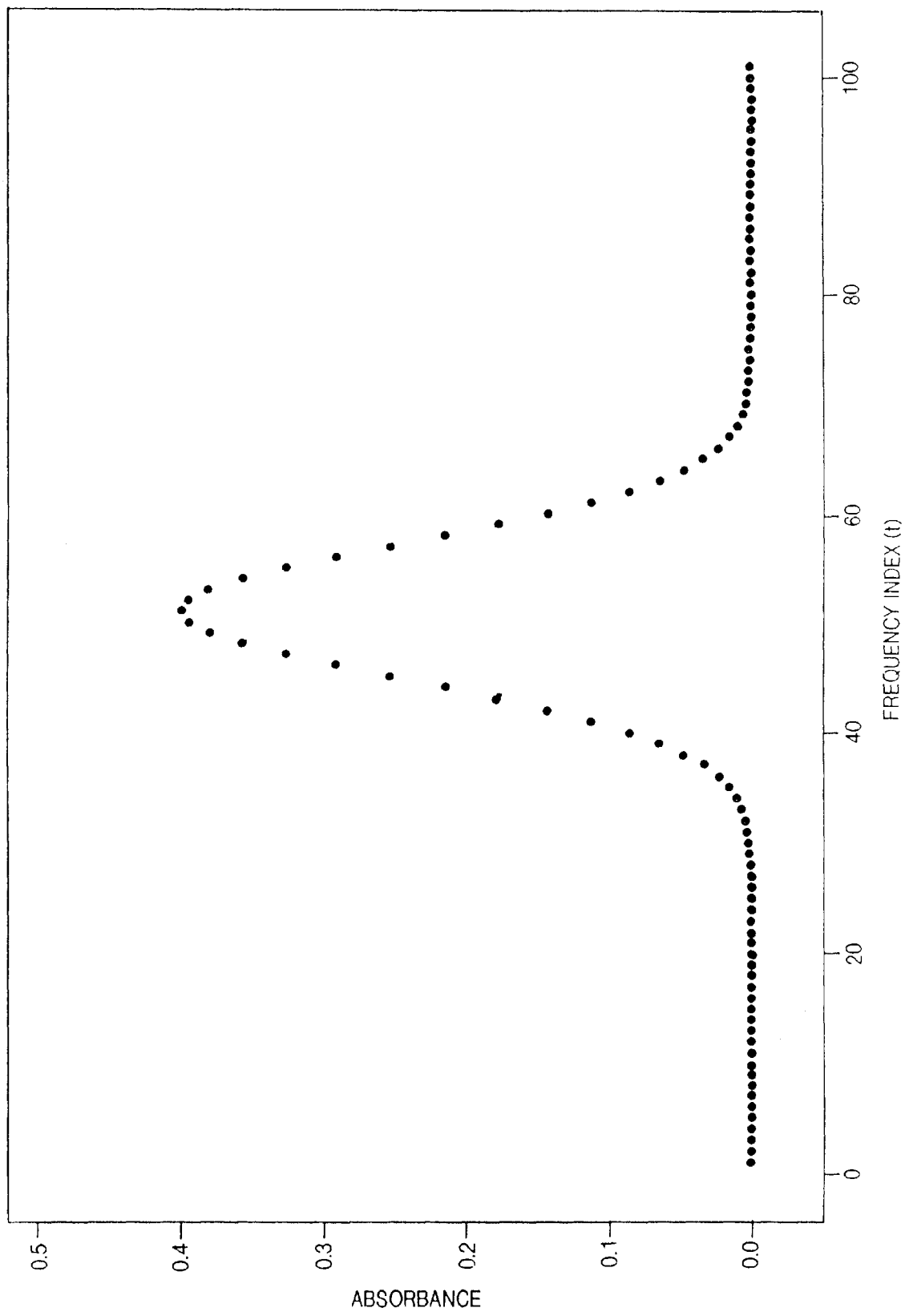
FIG. 1 illustrates a Gaussian absorbance spectrum.
Figure 3A:
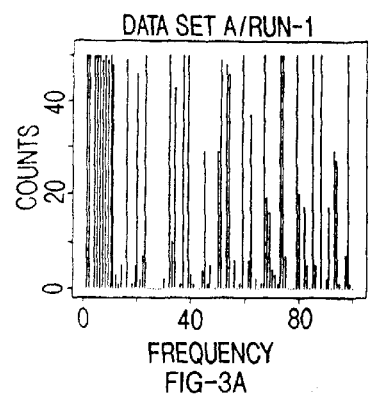
FIGS. 3A–3L illustrates the count spectra associated with $G^{40}$ for each genetic algorithm run (and combined over all three runs) using the three synthetic data sets A, B, and C)
Figure 3B:
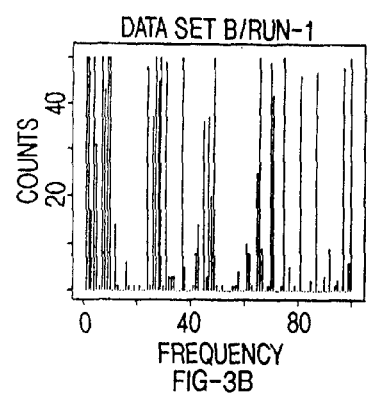
Figure 3C:
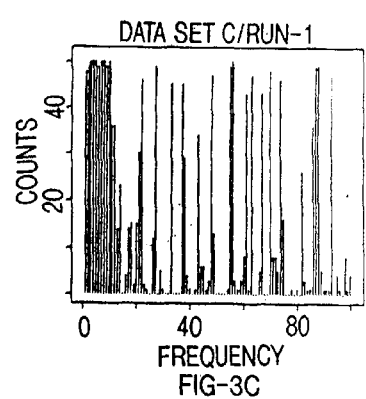
Figure 3D:
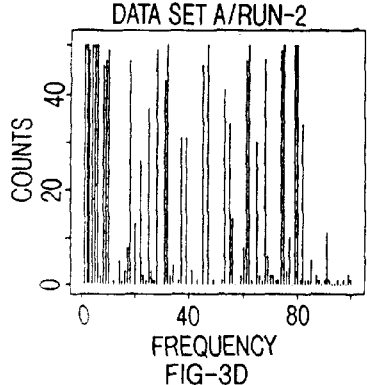
Figure 3E:
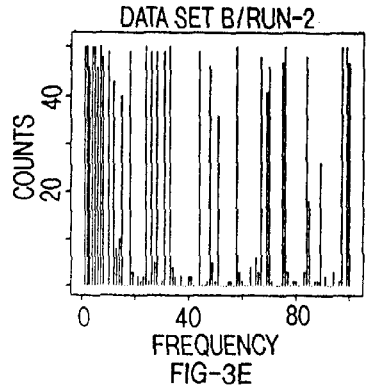
Figure 3F:
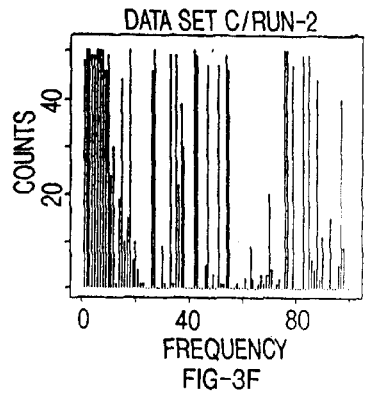
Figure 3G:
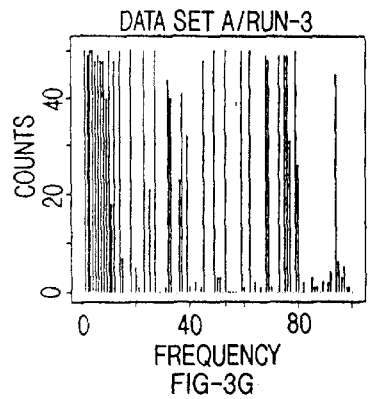
Figure 3H:
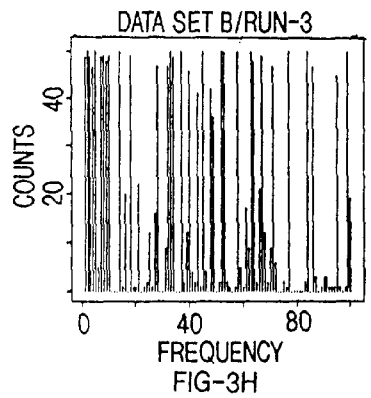
Figure 3:
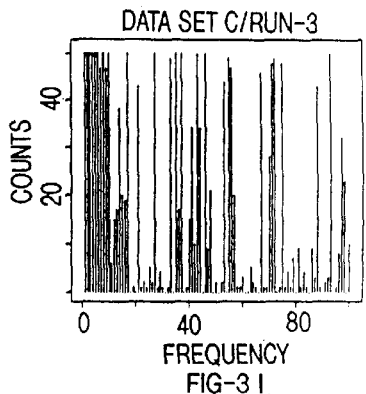
Figure 3J:
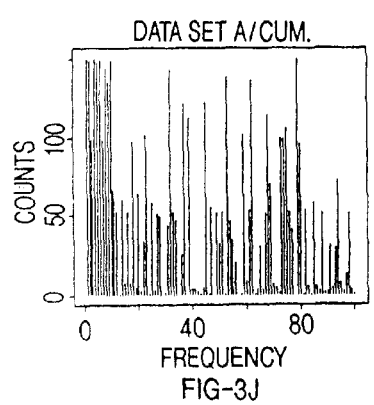
Figure 3K:
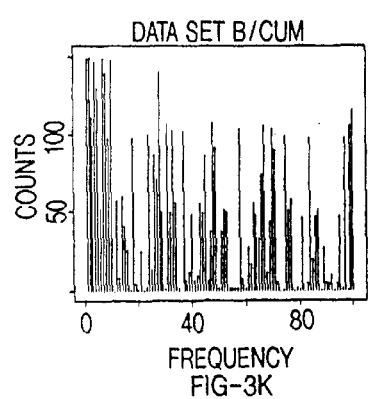

FIGS. 2 and 3 summarize the performance of the genetic algorithms over forty generations for each of the nine runs. The matrices of subplots in FIGS. 2 and 3 are organized such that each column of the matrices contains summaries of the three genetic algorithms runs associated with a single data set realization.

FIG. 2 presents the distribution of SEP versus generation for each run. For comparison, the PLS model performance is indicated for the following two cases: when all 100 wavelengths are used, and when only the 10 relevant wavelengths are used. The difference in performance between these two cases indicates significant improvement in performance with judicious wavelength selection. In general, within a genetic algorithm run, there is a wide variation in performance at the first generation. In fact, for each genetic algorithm run, models based on more than one-half of the wavelength subsets within G$^1$ result in performance that is poorer than if all 100 wavelengths were used. As the genetic algorithm processes evolve, performance generally improves and variability in performance decreases. In these cases, the performance has roughly converged by the 40th generation. The performances of wavelength subsets of G$^{40}$ are nearly at the level that would have resulted if only the 10 relevant wavelengths were used for modeling. The ability of the genetic process to find the near optimal set of wavelengths is important to recognize. Thus, for this example containing synergy, the genetic algorithm repeatedly evolved to wavelength subjects with near optimal performance (as measured by SEP).

FIG. 3 indicates the overall composition of the wavelength subsets associated with G$^{40}$ for each genetic algorithms run and overall for each data set realization. The subplots (denoted count spectra) comprising the first three rows of FIG. 3 indicate the number of times, out of fifty, that each wavelength appears in G$^{40}$ for the nine genetic algorithm runs. Each count spectrum in the fourth row indicates the cumulative number of times each wavelength appears in G$^{40}$ for the three genetic algorithm runs on each data set. The differences among the first three count spectra within a fixed column are indicative of the sensitivity of the procedure to the selection of G$^1$. On the other hand, the similarities among count spectra for a fixed column can be used to assess the effects of chance errors in spectral measurements that act constructively or destructively with respect to prediction. The tendency of the genetic algorithm to select relevant wavelengths and remove irrelevant wavelengths is clear. By the 40th generation, the 9 runs of the genetic algorithms produce wavelength subsets that contain most of the relevant wavelengths, most of the time. In contrast, only a relatively small number of the irrelevant wavelengths appear regularly for a given genetic algorithms run (see the fourth row of count spectra). Thus, for this example, we conclude that chance measurement errors do not lead often to the systematic inclusion of irrelevant wavelengths. Rather, due to the relatively small size of r, the initial specification of G$^1$ has a great influence on the specific irrelevant wavelengths that appear regularly after the process has settled down.

In combination, FIGS. 2 and 3 demonstrate the sensitivity of the genetic algorithms process to the particular data set. From FIG. 2, it is clear that the genetic algorithms processes involving data set C converged to wavelength subsets with relatively homogeneous performance. The result of this improved convergence is apparent in FIG. 3, where it is shown that every relevant wavelength appears in all (or nearly all) of the 50 subsets of G$^{40}$.

The summaries provided by the fourth row of count spectra in FIG. 3 suggest that it may useful to consider the combined behavior of a number of genetic algorithms runs when selecting wavelengths. Compared with individual genetic algorithms runs, note that there are fewer irrelevant wavelengths that appear often in the composite 40th generations. Similarly, compared with individual genetic algorithm runs, there are fewer relevant wavelengths that fail to appear regularly in the composite 40th generations. Thus, to assure that inclusion (exclusion) of relevant (irrelevant) wavelengths is maximized due to the effects of chance selection of G$^1$, multiple genetic algorithm runs should be used as the basis for selecting wavelengths.

A simple strategy for selecting wavelengths includes comparing the cumulative number of times (over multiple genetic algorithms runs) that wavelengths appear in the final generation with various threshold values. Associated with each threshold value (T) is a set of wavelengths which can be represented by a binary string, $S(T)=\{I_1(T), I_2(T), \ldots, I_q(T)\}$. $I_j(T)=1$ if the $j^{th}$ wavelength appears at least T times; otherwise $I_j(T)=0$. A reasonable metric to evaluate the performance of the wavelength subset defined by T is the SEP (S(T)) obtained by cross-validation.

TABLE 2

Attributes of S(T) versus T $$SEP, q = \sum_{j=1}^{100} I_j(T), q^* = \sum_{j=1}^{10} I_j(T).$$

| | Data Set A | | | Data Set B | | | Data Set C | | |
|---|---|---|---|---|---|---|---|---|---|
| T | SEP | q | q* | SEP | q | q* | SEP | q | q* |
| 0 | .143 | 100 | 10 | .151 | 100 | 10 | .129 | 100 | 10 |
| 20 | .039 | 58 | 10 | .066 | 59 | 10 | .068 | 61 | 10 |
| 40 | .059 | 50 | 10 | .056 | 51 | 10 | .062 | 54 | 10 |
| 60 | .029 | 30 | 10 | .034 | 61 | 9 | .041 | 35 | 10 |
| 80 | .027 | 25 | 10 | .033 | 28 | 9 | .031 | 23 | 10 |
| 100 | .029 | 20 | 8 | .024 | 19 | 8 | .028 | 17 | 10 |
| 120 | .028 | 14 | 8 | .017 | 8 | 7 | .030 | 16 | 10 |
| 140 | .036 | 9 | 7 | .022 | 7 | 6 | .031 | 13 | 10 |
| Benchmark* | .032 | 10 | 10 | .028 | 10 | 10 | .041 | 10 | 10 |

*Only the relevant wavelengths are used

For each of the three data sets, Table 2 (above) provides the SEP along with two other attributes of S(T): (1) the total number of wavelengths in the subset defined by T, $$q = \sum_{j=1}^{100} I_j(T);$$

and (2) the number of relevant wavelengths in the subset defined by T, $$q^* = \sum_{j=1}^{10} I_j(T).$$

Notice that for all three data sets, the SEP steadily drops until T reaches 60 or 80. At this point, the SEP remains relatively constant. Also, note that S(80) contains nine (data set B) or ten (data sets A and C) of the ten relevant wavelengths. Conversely, S(80) contains only about 15% of the 90 irrelevant wavelengths in all three cases. Thus, a threshold of 80 successfully eliminates most of the irrelevant wavelengths, while maintaining most of the relevant wavelengths. Increasing T beyond 80 eliminates additional irrelevant wavelengths at the expense of eliminating relevant wavelengths. If T is increased to 140, the performance begins to degenerate. In summary, determination of the threshold that minimizes SEP will result in the selection of relevant wavelengths and omission of irrelevant wavelengths so as to improve the performance of the multivariate algorithm.

The magnitude of the effects of chance errors in spectral measurements that act constructively with respect to prediction can be assessed by comparing the benchmark SEP's (see Table 2, above) with the SEP's of wavelength subsets associated with T≧100. True future performance is optimized when only the 10 relevant wavelengths are used. For all data sets, an improved (lower) SEP is achieved when irrelevant wavelengths are included. Thus, this demonstrates that the SEP can be an overoptimistic measure of performance when used in this context. Nevertheless, it can lead to selection of a near optimal set of wavelengths. If a more realistic measure of performance is needed, one could proceed as follows: (1) select wavelengths using one-half of the data set; and (2) evaluate performance using the other half of the data set in conjunction with the set of wavelengths obtained in (1). Some important factors that affect the level of overoptimism are the number of calibration factors, the number of candidate wavelengths, and the true optimal performance level of the model. In this example, the relatively small number of calibration samples was responsible for this overoptimism.

A summary of the basic strategy for optimal wavelength selection is as follows. First, summarize the results of multiple genetic algorithms runs, as in the fourth row of FIG. 3. Second, evaluate SEP (S(T)) for various levels of T. Third, find the level of T, $T_{opt}$, that minimizes SEP (S(T)). Select $S(T_{opt})$ as the set of wavelengths to be used to develop a model which can be used to predict analyte concentrations of future specimens. This basic strategy can be modified by subject matter and economic considerations, but it provides a unique, powerful, and proven method for wavelength selection.

To further illustrate the capabilities of these methods the following example demonstrates simultaneous wavelength selection and cost minimization. With reference to a noninvasive glucose monitor, a number of experiments on various model solutions have been performed. The purpose of one of these experiments was to evaluate the ability to estimate the concentration of glucose in aqueous solutions containing two other components (i.e., urea and alcohol) commonly found in biological fluids in the presence of significant temperature variation. Thirty-two aqueous solutions with various concentrations of each of the three components were prepared. The set of solutions was designed so that there was virtually no correlation among the concentrations of different components. The concentration of glucose in these solutions ranged from 0 mg/dL to 990 mg/dL. The absorbance spectra of these solutions were obtained in the near-infrared region from 914 nm to 1324 nm at a fixed wavenumber ($cm^{-1}$) interval. Solution temperatures were intentionally varied to make the development of a calibration model more difficult. The pattern of temperature variation was controlled so that there was no significant correlation between temperature and the component concentrations. As is common in the analysis of near-infrared spectra, the absorbance spectra were smoothed and then differenced. Smoothing was accomplished by using a 15-point moving average filter. First-order differencing was applied to the smoothed spectra.

Figure 4:
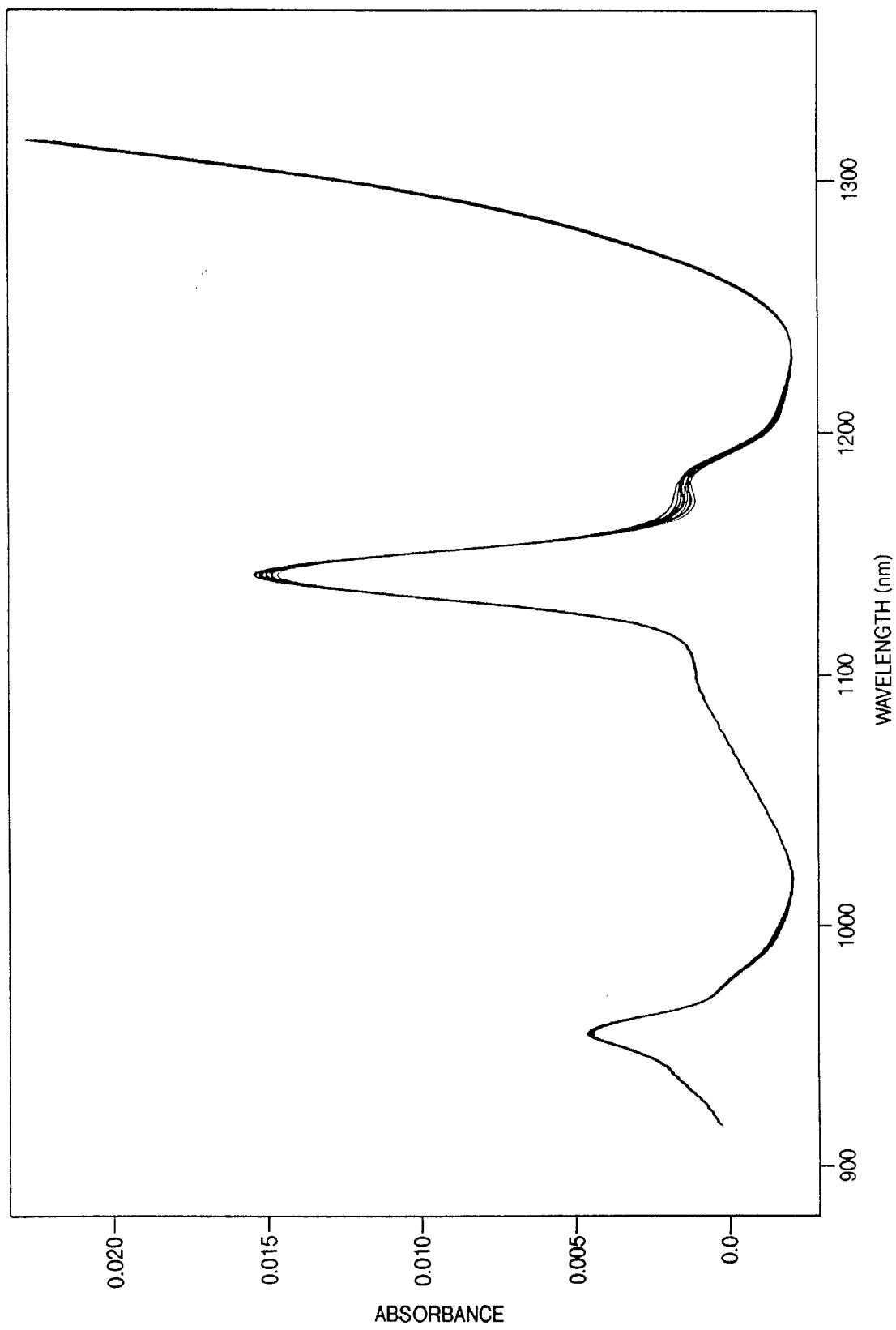
FIG. 4 illustrates the near-infrared spectra (smoothed and differenced) of model aqueous solutions at constant wavenumber resolution.
Figure 5A:
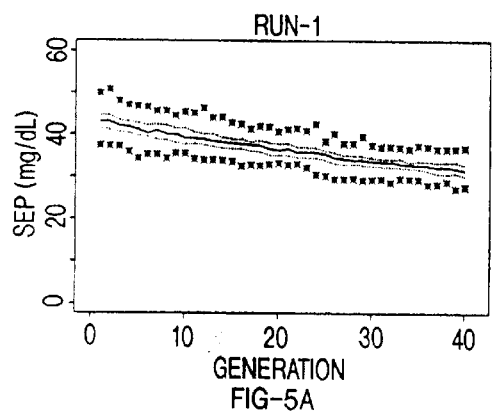
FIGS. 5A–5H is a summary of the individual performances of each of the four genetic algorithm runs on the near-infrared spectral data of aqueous solutions, wherein the distribution of the SEP versus generation is on the left, and the $G^{40}$ for each genetic algorithm run are on the right.
Figure 5B:
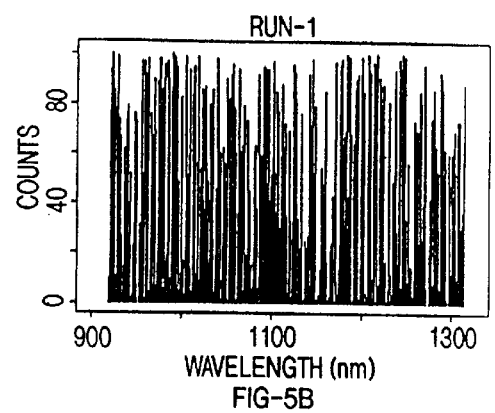
Figure 5C:
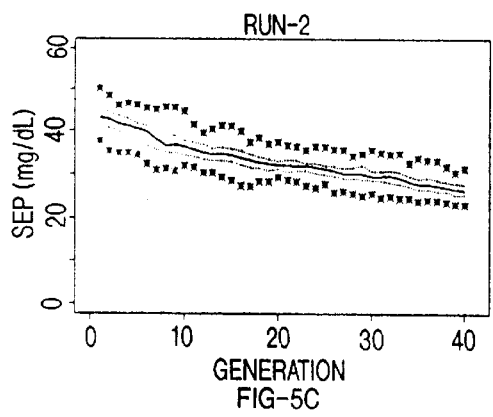
Figure 5D:
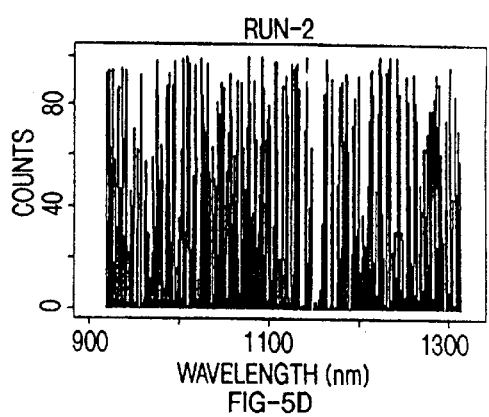
Figure 5E:
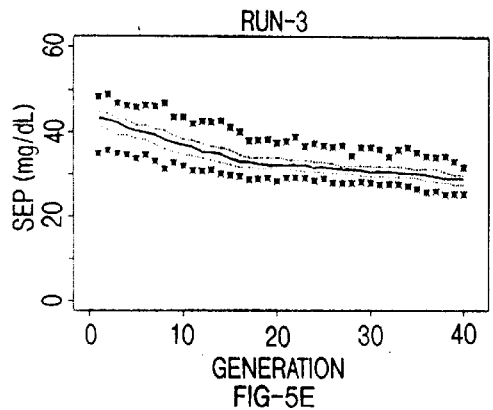
Figure 5F:
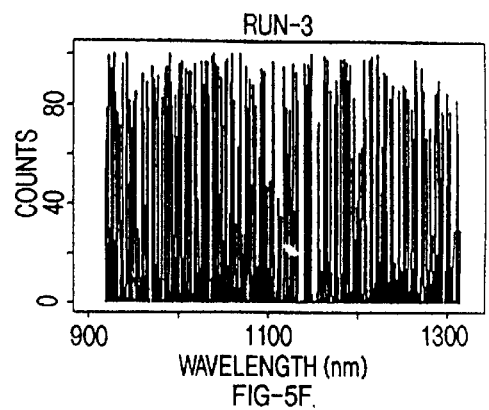
Figure 5G:
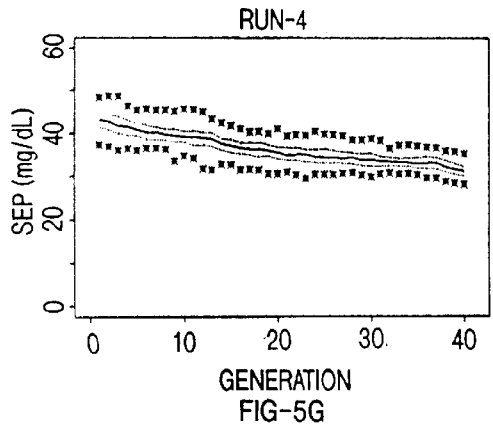
Figure 5H:
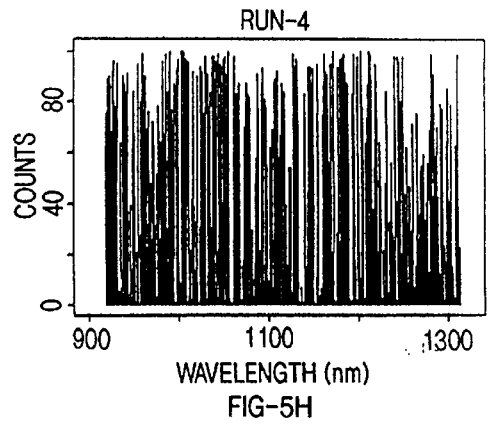

The smoothed and differenced spectra (see FIG. 4), in combination with the known glucose concentrations, were used to develop various calibration models with PLS. When all wavelengths (q=440) are used, the optimal model size (10 factors) was found by using n-fold cross-validation. The SEP associated with this PLS model involving all wavelengths was 42.4 mg/dl. This method of processing is the current standard practice, as evidenced in by the published prior work of Robinson ("Noninvasive Glucose Monitoring in Diabetic Patients: a Preliminary Evaluation", M. R. Robinson, R. P. Eaton, D. M. Haaland, G. W. Koepp, E. V. Thomas, B. R. Stallard and P. L. Robinson, *Clinical Chemistry*, Vol. 38, No. 9, 1992, pages 1618–1622), and the recent article Marbach, et al., (August 1993). The methodologies disclosed in these articles do not utilize wavelength selection to improve the performance of the multivariate measurement.

The same spectral data were subsequently processed utilizing the genetic selection process described herein. Four different variations of $G^1$ were used to initiate four genetic algorithm runs using these data. The model size was fixed to 10 factors throughout the optimizations. For each run, the operational parameters of the genetic algorithm were $p_m=0.005$, $r=100$, and $$F = \frac{1}{q} (SEP)^{-4}$$

where q represents the number of wavelengths measured. It is important to note that the fitness function includes terms that could relate to both performance and cost. The cost component is implemented through the 1/q factor in the fitness function. For many optical instruments there is a cost associated with each wavelength measured. Thus, the particular form of the fitness function used in this example incorporates both cost and performance considerations. This fitness function should be beneficial in removing wavelengths that do not affect performance greatly one way or another. Due to massive computational requirements, only 40 generations were developed for each genetic algorithm run. Each run of the genetic algorithm required 46 hours of VAX-8600 CPU time.

FIG. 5, summarizes the individual performance associated with each of the four genetic algorithm runs. There is steady, but slow improvement in performance during the evolution of each of the four genetic algorithm runs. While additional improvement in performance appears possible by allowing the genetic algorithms runs to continue further, the computational requirements offer a significant impediment. Comparison of the overall compositions of the wavelength subsets associated with $G^{40}$, from run to run, is difficult.

Figure 6:
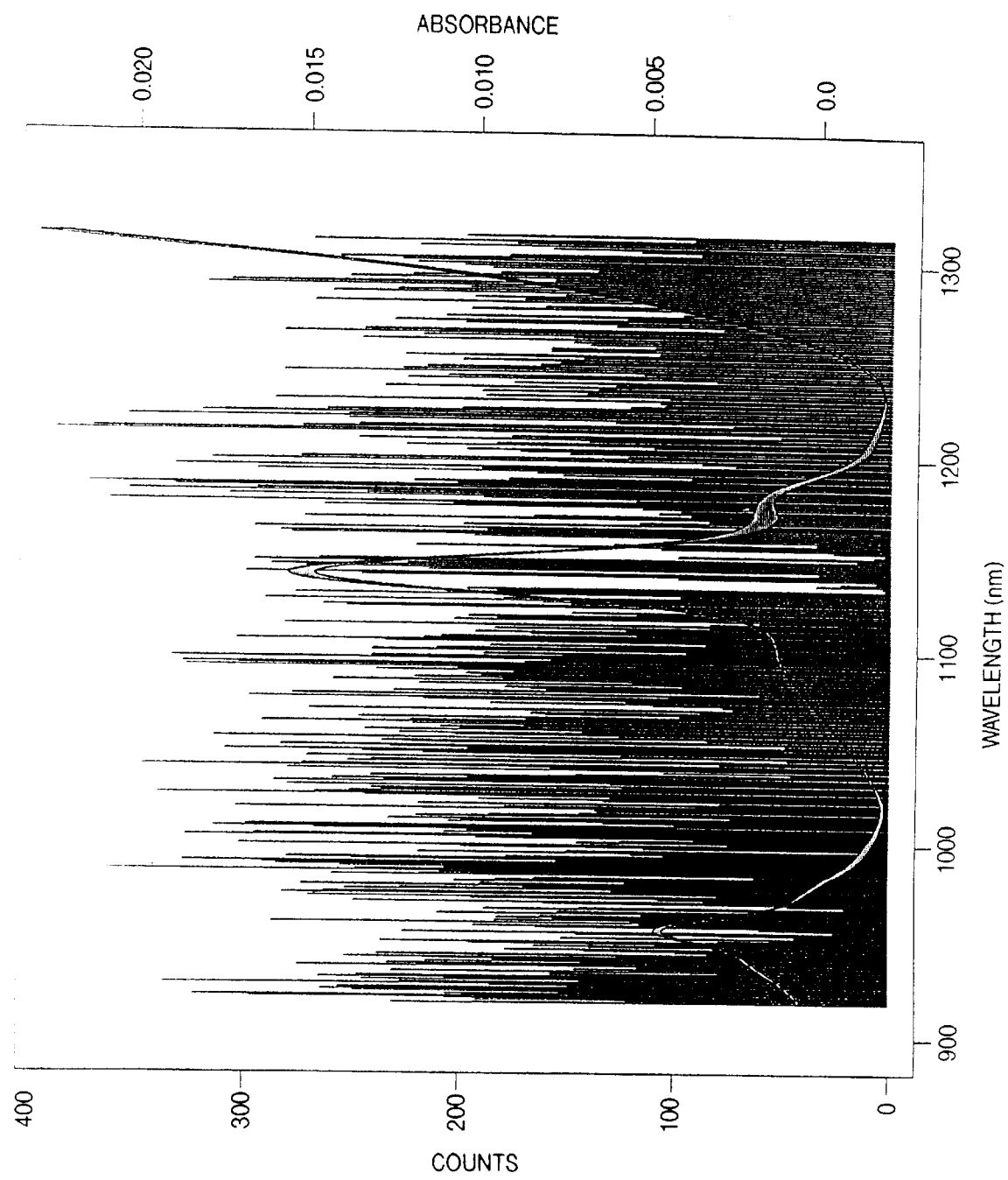
FIG. 6 illustrates the count spectrum (combined over all four runs) for $G^{40}$, over which is superimposed a filled polygon indicating the range of the smoothed and differenced near-infrared spectra of aqueous solutions.
Figure 7:
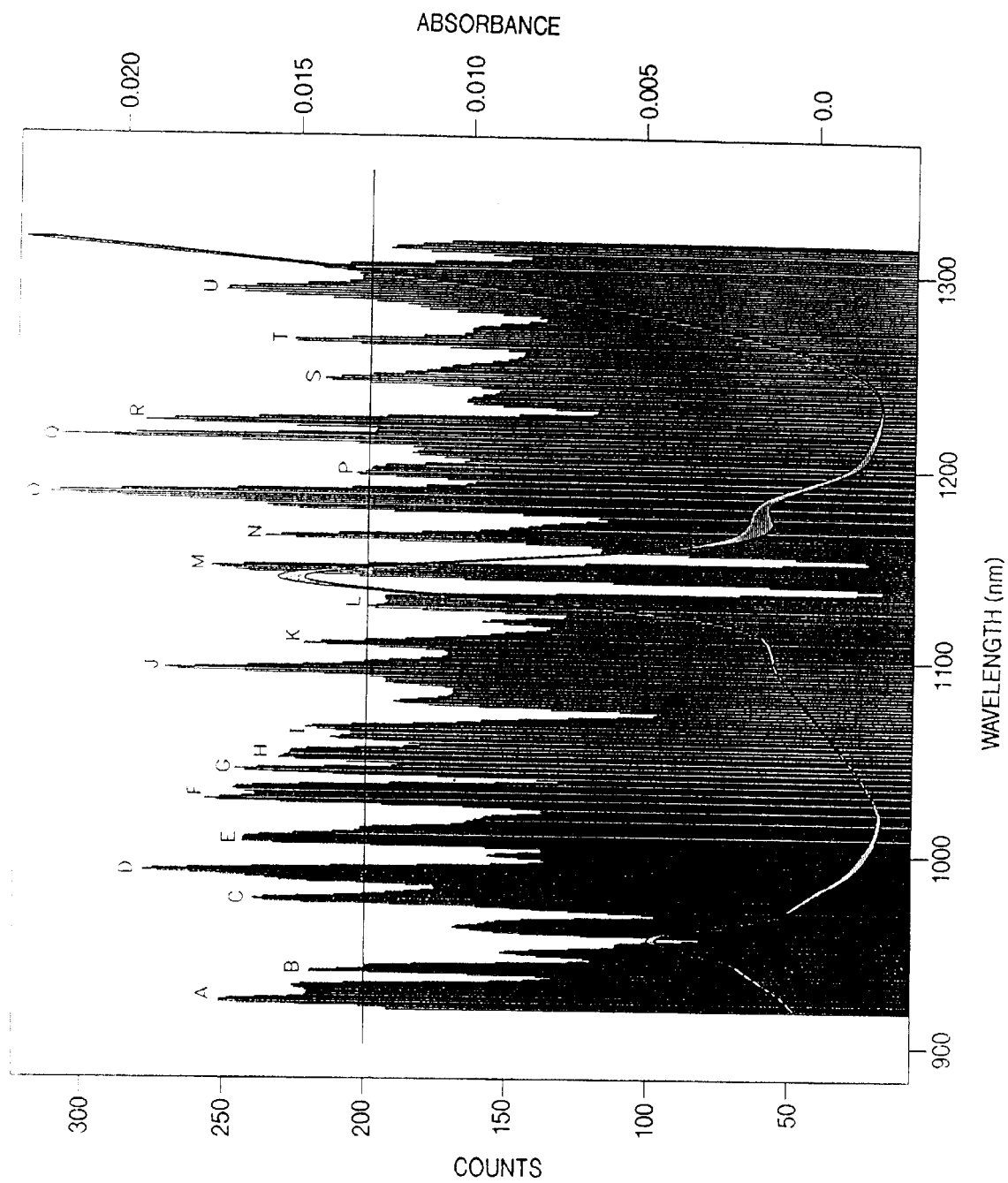
FIG. 7 illustrates the smoothed count spectrum (combined over all four runs) for $G^{40}$ with the filled polygon associated with the transformed near-infrared spectra, and wherein the 21 spectral regions associated with at least 200 smoothed counts are identified by A, B, . . . , U.

The commonalities among the $G^{40}$ wavelength subsets are illustrated more clearly in FIG. 6. From this figure, we can see regions that are useful for modeling glucose (e.g., ≈1180 nm) and other regions that appear to inhibit modeling (e.g., ≈1130 nm and ≈1150 nm). Nevertheless, there is still a certain amount of local sharp irregularity that is inconsistent with the inherent continuity of the spectral features of the components in solution. In order to facilitate interpretation, a nonlinear smoother known as 4(3RSR)2H (see Tukey, J. W., *Exploratory Data Analysis*, Addison-Wesley, Reading, Mass. (1977)) was applied to the count data in FIG. 6 to form the smoothed count data displayed in FIG. 7. Note that the span of this filter is relatively small when compared to the widths of the spectral features associated with the components in solution. Thus, use of this smoothed representation of the genetic algorithm output for interpretation is justified due to the fact that if a spectral wavelength is important for modeling, then its most local neighbors should also be important. Note also that other smoothers could be as effective as 4(3RSR)2H.

Figure 8:
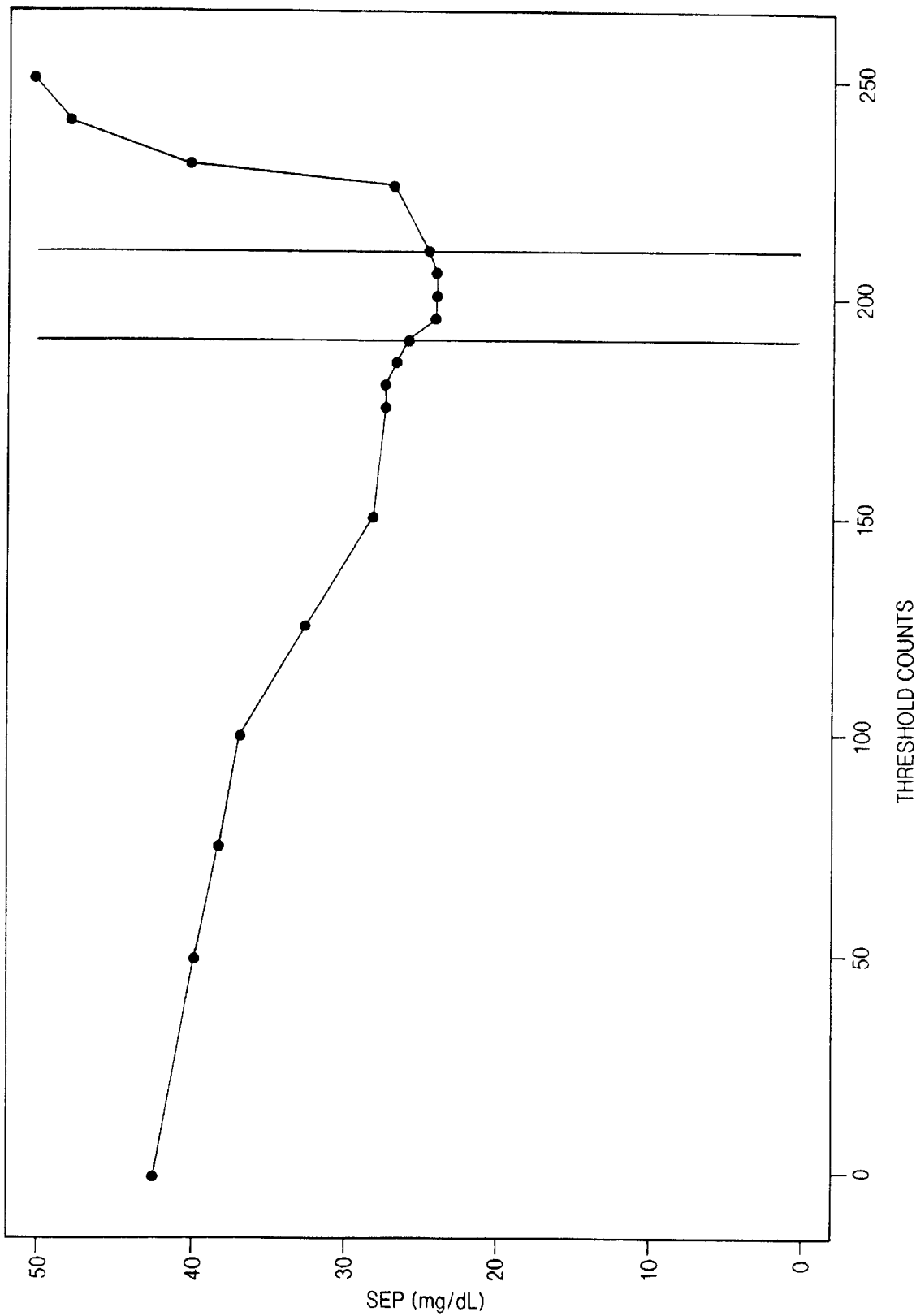
FIG. 8 illustrates SEP(S(T)) versus T, wherein S(T) is based on the smoothed counts illustrated in FIG. 7.

Consistent with the strategy recommended in the previous section, SEP (S(T)) was evaluated for various levels of T. Here, S is defined in terms of the smoothed count data displayed in FIG. 7. From FIG. 8, which presents SEP (S(T)) versus T, we find that a reasonable choice of $T_{opt}$ is in the range from 190 to 210. Due to the physical considerations posed earlier, it is much easier to defend the use of smoothed (rather than raw) counts to construct wavelength subsets. Use of smooth counts also provides some comfort that the overoptimism associated with the various SEP's is relatively small. Thus, there should be no question that performance is significantly enhanced (with respect to using all wavelengths) by using sets of wavelengths defined by $T_{opt}$ $\epsilon$ [190, 210]. If we select $T_{opt}=200$, $S(T_{opt})$ defines 21 important spectral regions for modeling, (identified by A, B, . . . , U in FIG. 7). It is important to emphasize that important spectral regions do not necessarily relate directly to the component of interest. Rather, as in the example associated with Equation 6, these important regions may relate to interfering components. Here, some of the regions defined by S(200) relate to glucose, some relate to interfering components, and yet others remain unidentified, perhaps relating to complex effects of solution temperature on the spectra.

It is important to note that wavelength selection need not stop at this stage. Since we have reduced the number of spectral regions to a manageable number, we could evaluate the performance of various subsets of the important wavelength regions identified. For this example, performance (SEP) is optimized by omitting the following spectral regions: B, G, K, I, N, P, and Q. The SEP achieved by using the remaining 14 regions is 21.9 mg/dL, which is somewhat smaller than the 23.8 mg/dL SEP obtained when all 21 regions are used. Further reduction in number of spectral regions needed for modeling is possible without much loss in performance.

It is important to understand the enormous improvement realized by the foregoing steps. The standard method of multivariate processing used 440 wavelength measurements and yielded a SEP of 42.4 mg/dl. In comparison to the standard state of the art results, the results obtained by methodology which includes genetic selection utilized only 14 wavelength measurements and yielded a SEP of 21.9 mg/dl. Thus, the reduction in the standard error of prediction is more than a factor of 2 and the number of wavelength measurements used is reduced by a factor of 31. In the design of optical instrumentation, such improvements in performance and reduction in cost have tremendous commercial ramifications.

Figure 9:
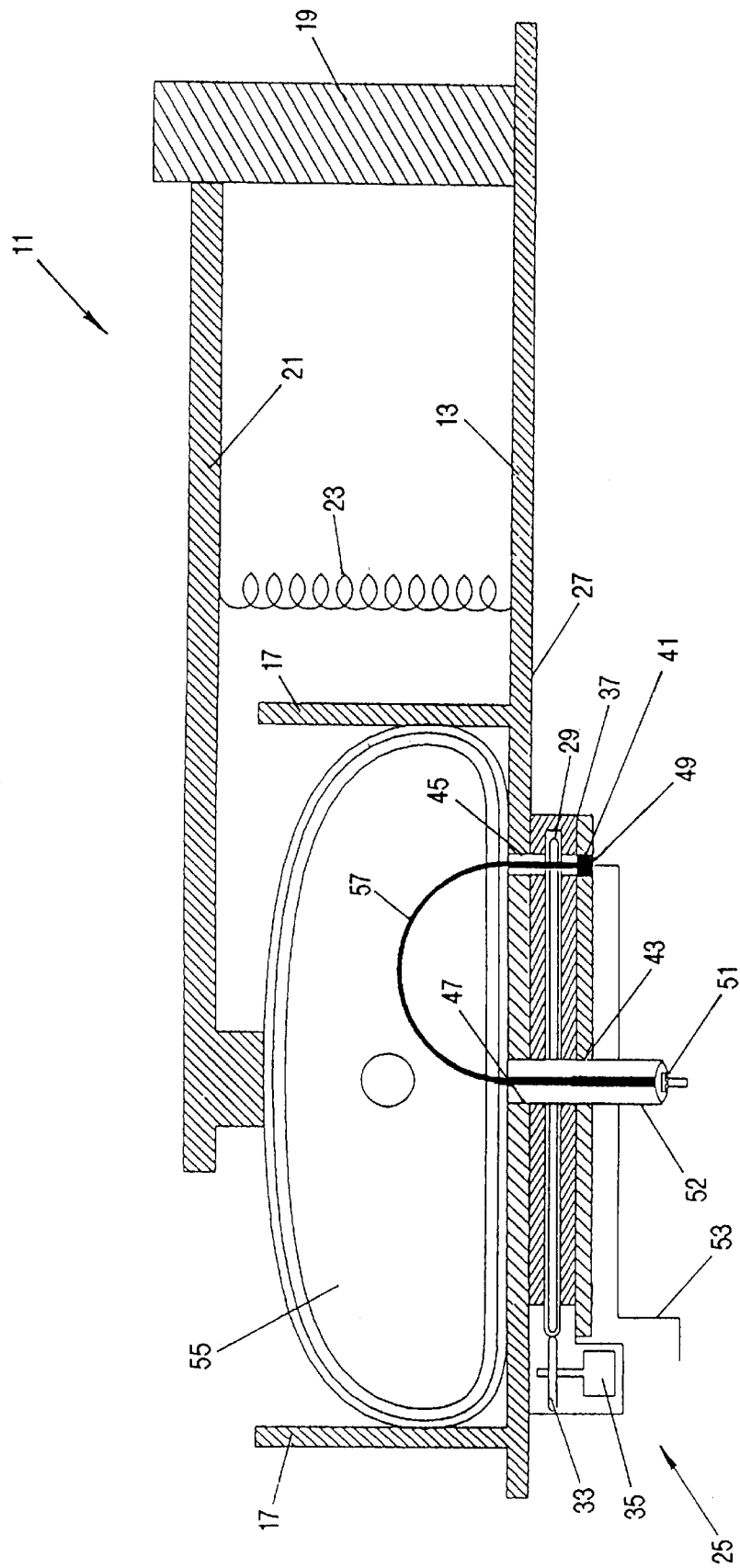
FIG. 9 is a schematic of a finger sampling device with a filter wheel.
Figure 10:
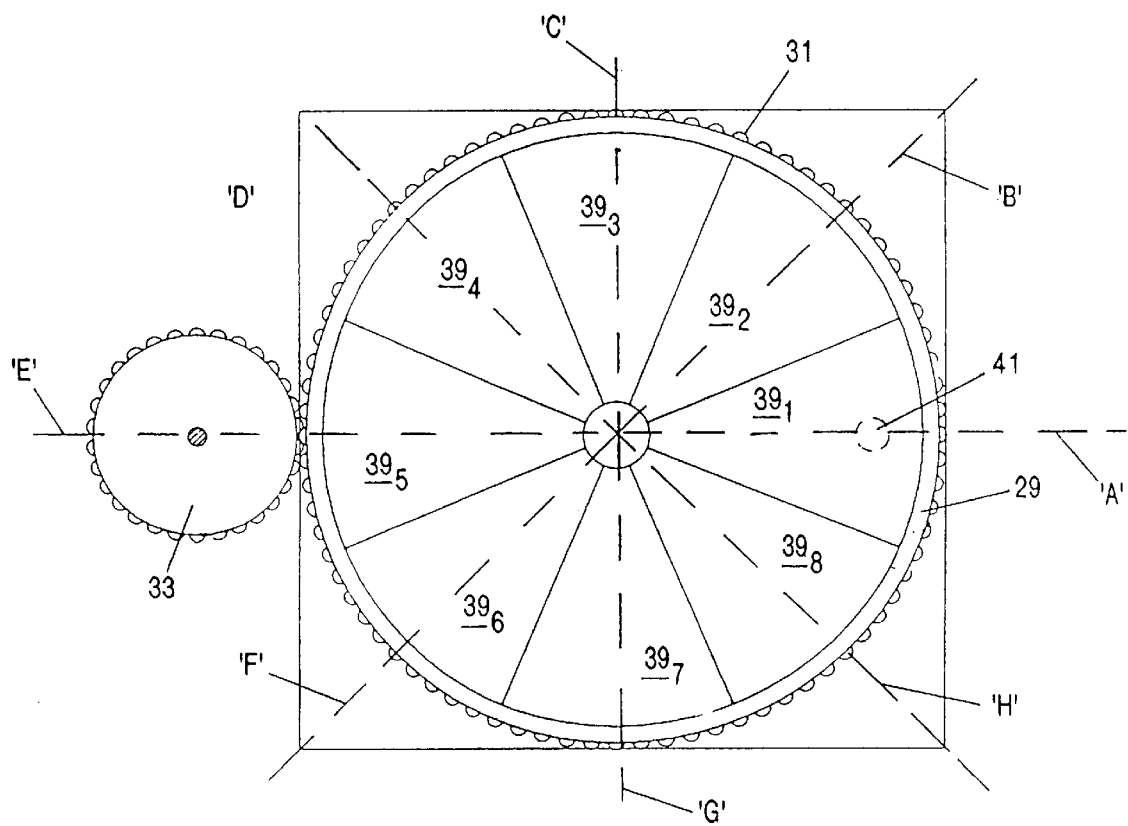
FIG. 10 is a top view of the filter wheel of FIG. 9.
Figure 11:
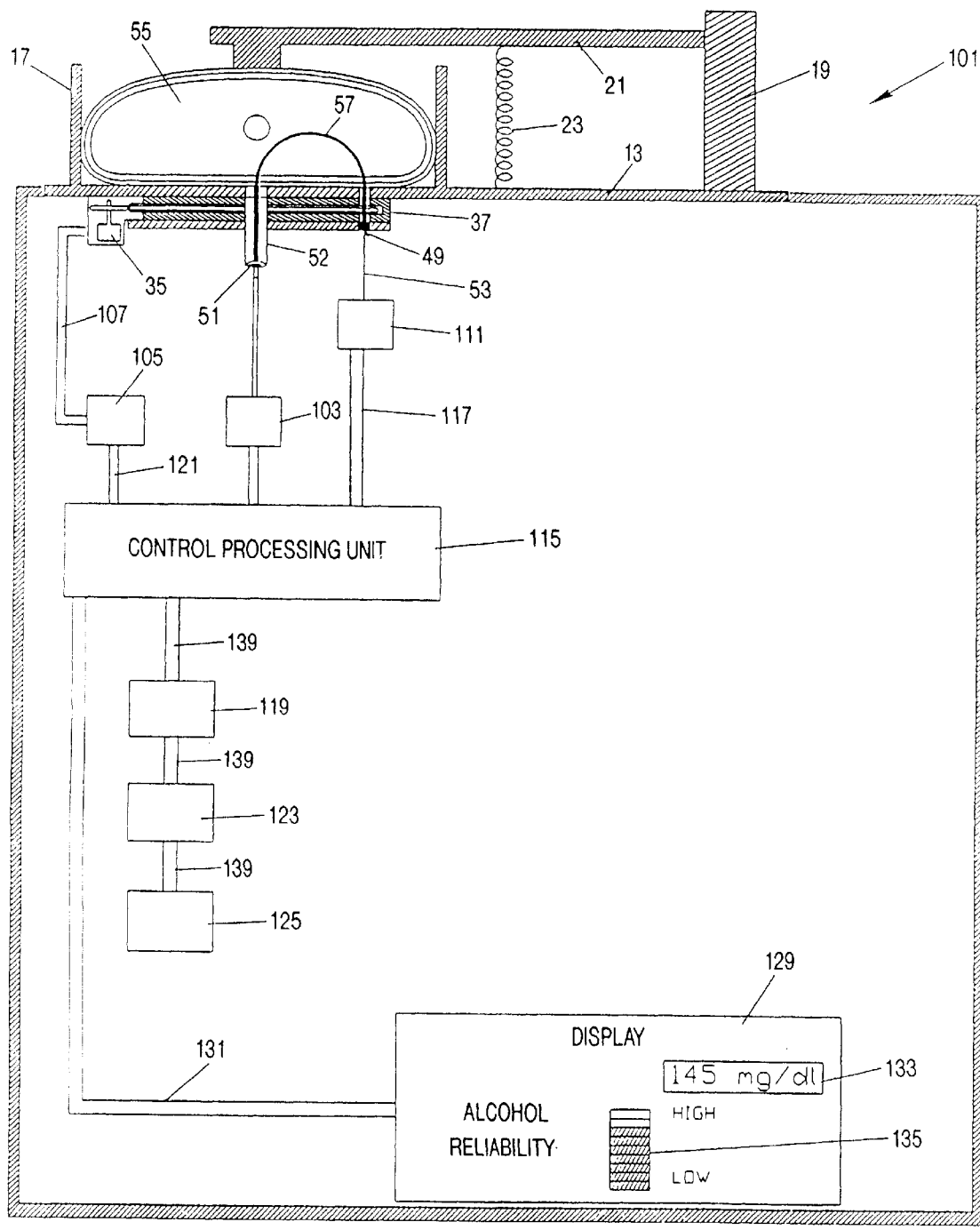
FIG. 11 is a schematic view of a noninvasive alcohol monitor incorporating the finger sampling device of FIGS. 9 and 10.

Over the past several years there has been an increasing interest in developing technology which could reduce the number of drunk driving fatalities. One problem with implementing any program is the current lack of an easy and reliable measurement of blood alcohol levels. A noninvasive infrared based blood alcohol monitor will provide the public with easily obtained and accurate results. FIGS. 9 and 10 illustrate a finger sampling device including a filter wheel. FIG. 11 illustrates how the components of FIGS. 9 and 10 are incorporated into a functional alcohol monitor.

Finger sampling device 11 includes a base 13, having a finger support surface 15, a pair of guide rails 17, and a post 19. Device 11 also includes an arm 21, which is hinged (by structure not shown) to post 19 and biased toward surface 15 by spring 23. Filter wheel assembly 25, which is secured to surface 27 of base 13, includes a rotating filter wheel 29 (having gear teeth 31 on the perimeter thereof), gear 33, and stepper motor 35. Filter wheel 29, which is supported by housing 37 in any convenient manner (not shown) is provided with 8 band pass filters $39_{1-8}$, each of which passes a discrete set of wavelengths (i.e., a wavelength subset) $\lambda_1, \lambda_2, \lambda_3 \ldots \lambda_8$. The number, resolution and spectral location of these filters being determined by the methodology set forth above, including the use of a genetic algorithm, to improve performance as well as reduce instrument cost. Note, while eight different filters are shown, the exact number could change based upon the fitness function used. Housing 37 also includes peripheral opening 41 and central opening 43 (which are aligned with openings 45 and 47 in base 15). As illustrated, detector 49 is positioned in the lower end of opening 45. Light source 51 is positioned relative to aligned openings 43, 47. Detector 49 is connected to an analog to digital converter via signal line 53.

In operation, light is introduced into finger/thumb 55 via broad band source 51 via light pipe 52, a portion of which is partially transmitted as indicated by path 57. Of that light transversing path 57 and continuing through opening 45, only the light of the appropriate wavelength subset $\lambda_1$ will pass through filter $39_1$, and is detected by detector 49. As filter wheel 29 has eight discrete positions (i.e., A–H), once the intensity of wavelength subset $\lambda_1$ have been measured, stepper motor rotates wheel 29 from the position illustrated in FIG. 10 to the position where position B is aligned with detector 49. In this position the intensity of wavelength subset $\lambda_2$ is then measured. Wheel 29 is rotated through the remaining positions until all 8 wavelength subsets are measured.

FIG. 11 illustrates the major components of a noninvasive alcohol monitor 101 employing a broad band light source, filter wheel and detector. The optical sampling of finger/thumb 55 is performed with the same structure and in the same manner as previously discussed in reference to FIGS. 9 and 10. The optical illumination is performed by a broad band light source 51, typically a tungsten halogen source, which allows illumination of finger 55 through openings 43 and 47. The operation of source 51 is controlled by electronics 103. The light transversing the finger is subsequently filtered by band pass filters $39_{1-8}$ on filter wheel 29. In operation, filter wheel 29 is rotated by stepper motor 35 which, in turn, is coupled to driver electronics 105 via signal line 107.

In the preferred embodiment, detector 49 is composed of Indium Gallium Arsenide. Detector 49 receives the selected wavelength subsets and converts the light intensity into a series of electrical signals. These electrical signals, which correspond to the intensity values at the detector, are transmitted to electronics 111 via signal line 53. Within electronics 111 is an A/D converter.

The digital number corresponding to the intensity value at each wavelength subset from detector 49 are communicated from electronics 111 to central processing unit 115 via signal line 117. The digital intensity values are subsequently stored in memory module 119. Upon completion of the measurement at one wavelength subset, central processing unit 115 communicates with driver electronics 105 via signal line 121 and the filter wheel 29 is rotated. The preceding process is continued until all wavelength subsets have been recorded. Following measurement of all necessary wavelength subset values, these values are in module 119. Quantitative analysis of the wavelength subset values is performed by central processing unit 115 in conjunction with the multivariate calibration model and algorithms stored in module 123 and the stored wavelength subset values in module 119. The concentration value is subsequently displayed by unit 129, connected to central processing unit 115 via signal line 131. For example, alcohol concentration could be displayed in mg/dl units by display 133. Concurrent with the concentration determination, the wavelength subset values are examined to determine if they are similar to those used to generate the calibration model. If the values are unique or dissimilar from those used to develop the model then the accuracy of the measurement is poorly defined. The determination of measurement reliability is performed by central processing unit 115 while using the subset values stored in module 119 and outlier detection algorithms stored in module 125. The result of this analysis is displayed on reliability bar graph 135. Central processing unit 115, and modules 119, 123, and 125 are interconnected by signal lines 139.

Those people affected by diabetes must monitor the blood glucose levels several times daily in order to properly adjust their insulin therapy. A major limitation to the clinical goal of achieving ideal diabetic glucose control is the lack of unlimited and/or continuous glucose monitoring. Despite the non-invasive advances described in U.S. Pat. No. 4,975,581, a lancet cut into the finger is still necessary for all present forms of home glucose monitoring. This is so compromising to the diabetic patient that the most effective use of any form of diabetic management is rarely achieved. Thus, the need for a noninvasive glucose monitor is significant and the invention disclosed herein will facilitate realization of a monitor incorporating maximum performance and minimum cost.

Figure 12:
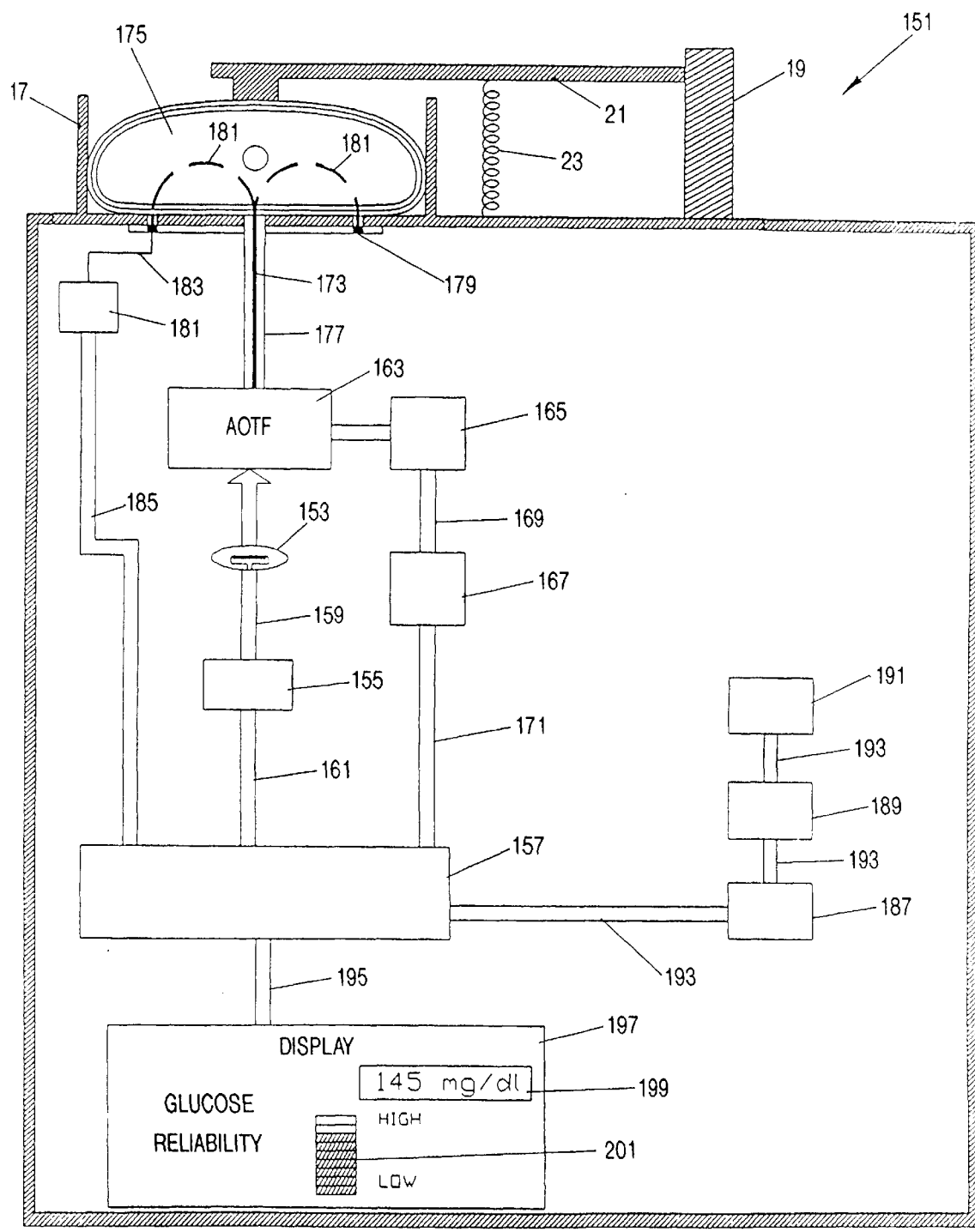
FIG. 12 is a schematic view of noninvasive glucose incorporating an AOTF.

FIG. 12 illustrates the major components of a noninvasive glucose monitor 151 employing a single broadband light source, an acusto optic tunable filter (AOTF), an appropriate finger sampling device, and detector. The broadband light source 153 is coupled to source electronics 155 which are in turn controlled by central processing unit 157 via electrical connections 159 and 161. AOTF 163 is coupled to central processing unit 157 via tunable rf source 165, AOTF driver electronics 167 and signal lines 169 and 171. The specific wavelength subsets transmitted by AOTF 163 are determined by the rf signals introduced onto the crystal by tunable rf source 165. The light 173 exiting AOTF 163 is incident on finger 175 via light pipe 177. The light propagates throughout the tissue with a portion exiting the tissue being incident on detector 179. A possible light path through the tissue is illustrated by paths 181. Detector 179 is annular in nature and allows for equidistant detection of the propagated light. The resulting analog signal from detector 179 is communicated to A/D converter 181 by signal line 183. The resulting digital values are communicated to central processing unit 157 via signal line 185. The values are then stored in memory storage unit 187. After a given wavelength subset is recorded, central processing unit 157 generates a signal to cause tunable rf source 165 to change the wavelength being generated, and the next wavelength subset is generated.

The physical and operational specifics of the AOTF are determined through use of the previously described steps. The physical specifics of the AOTF will include resolution and operational range. The operational specifics will include the specific wavelength subsets to be recorded, total measurement time, the amount of time a given wavelength subset to be recorded, and possibly the order in which they are recorded.

Following completion of the measurement the resulting wavelength subset values are processed in a manner similar to that previously described for FIG. 11. Noninvasive glucose monitor 151 includes memory storage unit 187, module 189 (in which are stored spectral processing algorithms and the multivariate calibration model), and module 191 (in which is stored the outlier detection algorithms). Memory unit 187 and modules 189, and 191 are interconnected via signal line 193. The result of the analysis is transmitted via signal line 195 for display by unit 197 as a specific value on display 199 and a bar graph 201 indicating reliability.

In 1965, 4.5% of all newborn deliveries in the U.S. were by Cesarean intervention. Today the rate has climbed to 25%. The marked increase in Cesarean delivery rate is the result of poor monitoring methods and the litigious nature of society. It has been estimated that 10% of all Cesarean deliveries are unnecessary, and the obstetrical community believes the Cesarean delivery rate could be decreased if the physiological status of the fetus was known. With technology currently available to the obstetrician, critical information concerning the most important physiological parameter of fetal well being, oxygen saturation, is not available. A monitor providing the ability to noninvasively and continuously measure oxygen saturation during the delivery process is disclosed in pending application Ser. No. 07/729,452.

Figure 13:
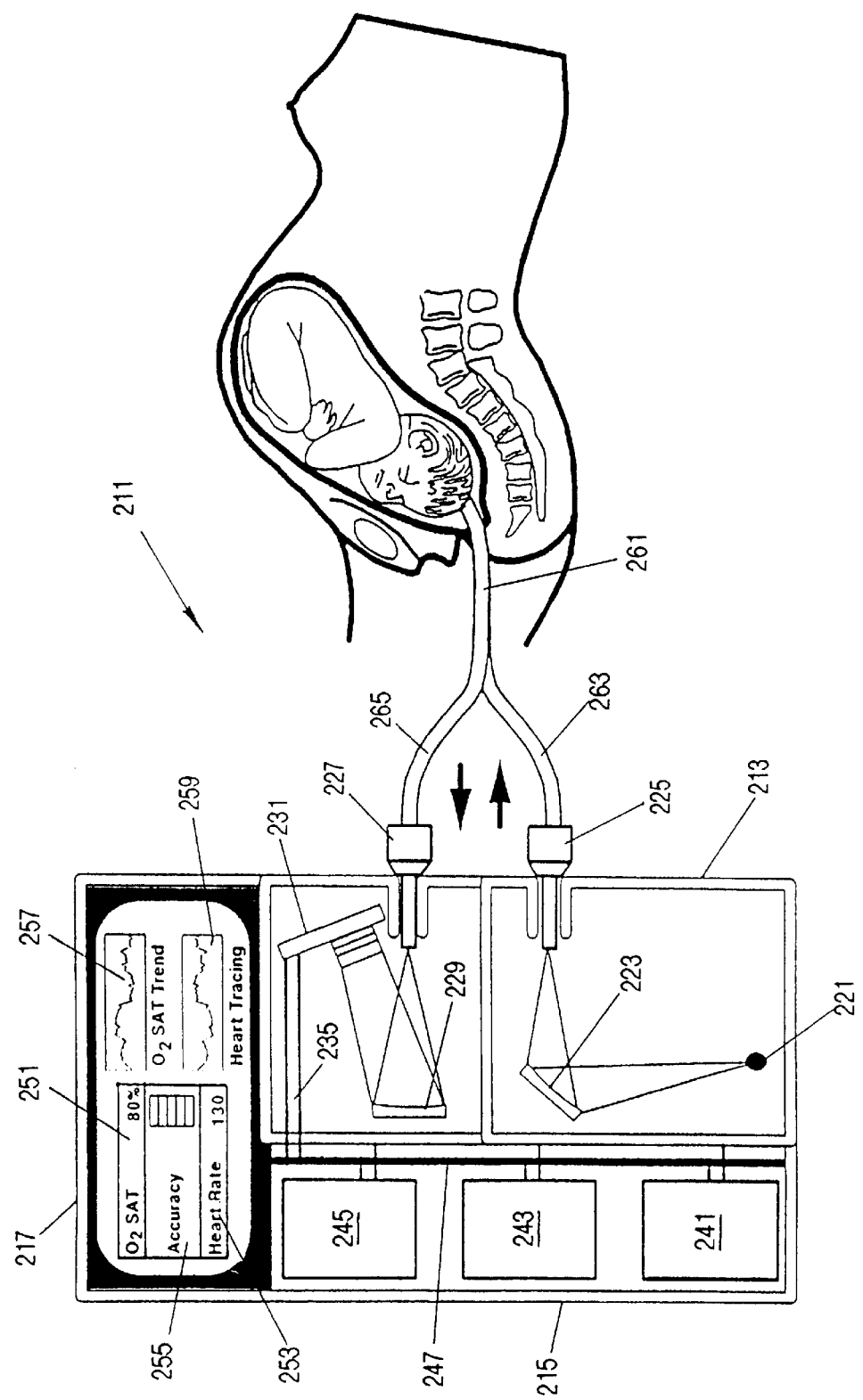
FIG. 13 is a schematic view of a fetal oximeter incorporating the improvements of the present invention.

With reference to FIG. 13, oximeter 211 includes a spectrometer 213, an electronics and computer processing module 215, and a visual display module 217. Spectrometer 213 includes a broad band halogen light source 221, a concave focusing mirror 223 a fiber optic housing 225, a second fiber optic housing 227, a grating 229, a silicon array detector 231, and an electric buss 235.

Module 215 includes a microprocessor 241, memory 243 in which the multivariate calibration model is stored, and module 245 in which the outlier defection algorithm is stored. Microprocessor 241, memory 243 and module 245 are connected together via suitable electronic connectors, as illustrated schematically at 247. Visual display module 217 includes a blood oxygen saturation display 251, heart rate display 253, an indicator of reliability of determination 255, oxygen saturation trend 257, and heart rate tracing 259. Finally, apparatus 211 includes a fiber optic bundle 261, including a source or input fibers 263, and a bundle of detector or output fibers 265. The end of bundle 261 is secured to the scalp of the fetus via a suitable suction or other device.

Source 221 is a broad band source emitting wavelengths in the region of 500 nm to 1000 nm. This light is transmitted to the fetus via input fiber 263 to illuminate a blood containing part of the fetus, such as the scalp illustrated in FIG. 13. The back scattered or reflected light is then transmitted back to spectrometer 213 by fiber bundle 265. Alternately the same optical fiber or a secondary optical fiber could be utilized. The returning light is then separated into various wavelengths and detected by the linear array detector 231.

The reflected light intensities at the various wavelengths are then analyzed by computer 241 employing a multivariate algorithm (such as PLS or PCR) utilizing wavelength subsets, which are determined by the above-described methodology including use of the genetic algorithm and a calibration model. The wavelength subset values are analyzed to establish which values correspond with maximum concentration of blood (or maximum dilation) in the arterial system of the fetus, and which values correspond with minimum concentration or dilation of the arterial system. Processing of the appropriate spectral information generated during maximum and minimum dilation will result in a set of values corresponding to the additional amount of blood present due to the pulse pressure generated by the heart. The resulting values are then analyzed by a multivariate algorithm to provide the operator with blood oxygen saturation as indicated by 251.

In this instrument configuration, the major sections of the optical assembly will be specified through use of the genetic algorithms. Specifically the groove density of the grating, the number of array diodes, size of the array and diode size, and the spectral coverage of the optical detection assembly will be determined with the use of the genetic algorithm.

Arterial blood gas determination is the cornerstone of diagnosis and management of cardiopulmonary disease in the critically ill patient. The values from arterial blood gas analysis provide vital information about the adequacy of oxygenation, ventilation, acid-base balance and gas exchange in the lungs. Yet little has changed through the years to improve how serial blood gas analysis is accomplished.

As effective oxygenation and maintenance of acid-base balance in critically ill patients is necessary for survival, measurement of arterial blood gases is typically the most frequently ordered laboratory test in a hospital's intensive care unit. The standard arterial blood gas report contains the following information: pH, $PCO_2$, $PO_2$, $[HCO_3^-]$, and $O_2$ saturation. At the present time standard clinical practice requires arterial puncture for procurement of an arterial blood sample. The arterial puncture is painful to the patient and associated with a variety of potential complications. In addition to the invasive procurement of blood, the current process for analyzing the arterial blood sample blood gas is slow and does not afford real time patient management. Given the dynamic fluctuations in arterial blood gas values in critically ill patients, assessment of lung function and patient-care decisions based on old information can often be inaccurate.

Figure 14:
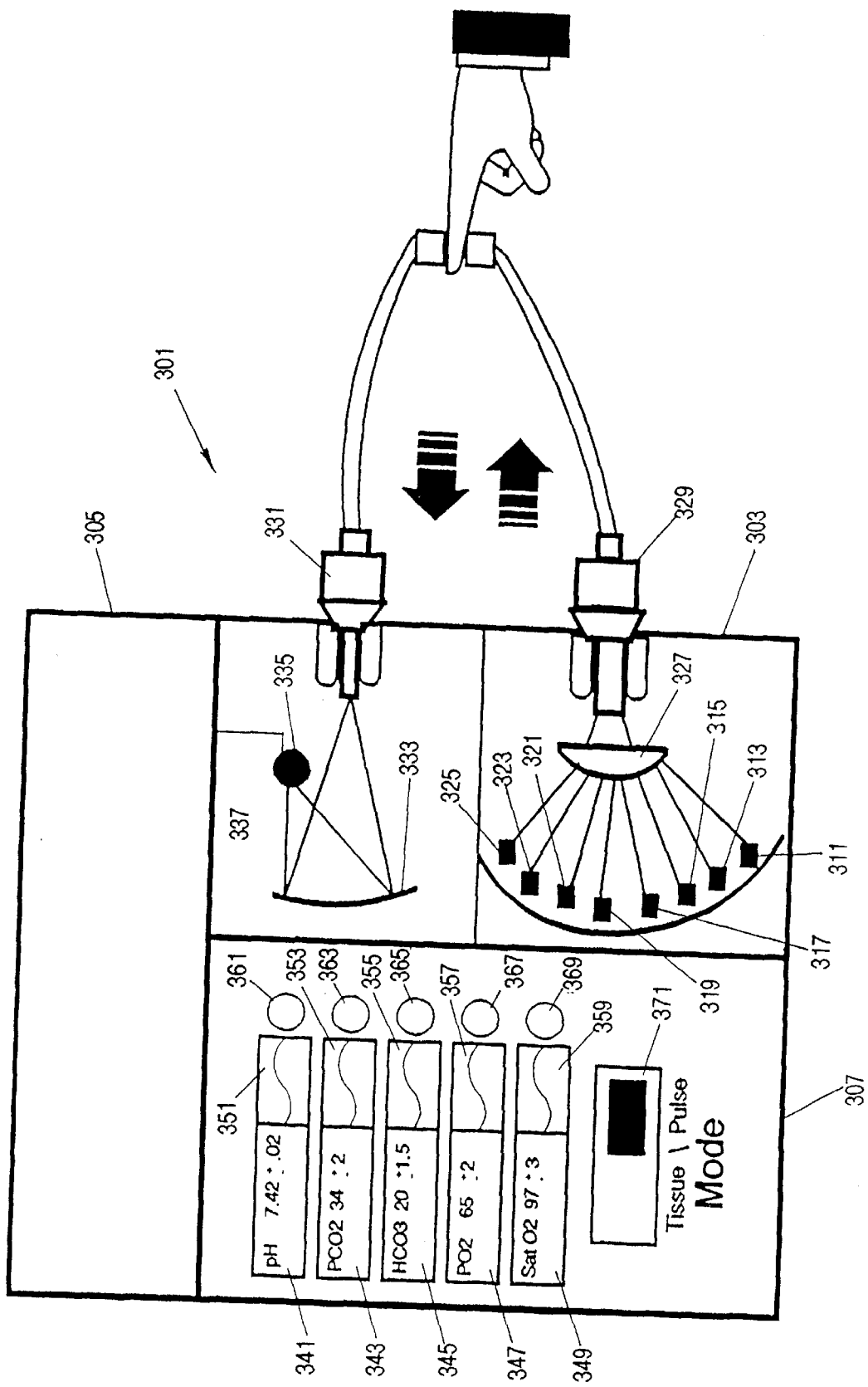
FIG. 14 is a schematic of a noninvasive blood gas monitor of the present invention.

Noninvasive arterial blood gas monitoring through the use of infrared spectroscopy is disclosed in pending U.S. application Ser. No. 07/910,004. An improved monitor is illustrated in FIG. 14. Noninvasive blood gas monitor 301 includes a spectrometer 303, an electronics and computer processing module 305, and a visual display module 307. Spectrometer 303 includes several light emitting diodes 311–325, a focusing lens 327, fiber optic interface 329, a second fiber optic interface 331, a focusing mirror 333, a detector 335, and an electronic buss 337.

Module 305 includes a microprocessor, a calibration model, a multivariate algorithm, and outlier detection methods. Visual display module 307 includes a pH display 341, a partial pressure of carbon dioxide display 343, a bicarbonate display 345, a partial pressure of oxygen display, 347, and an oxygen saturation display 349. Also included in module 307 are a pH trend display 351, a partial pressure of carbon dioxide trend display, 353, a bicarbonate trend display, 355, a partial pressure of oxygen trend display 357 and a oxygen saturation trend display 359. Visual display 307 also includes outlier lights 361–369 for each of the previous display analytes. Mode switch 371 permits the doctor or other operator to change the mode of instrument operation from tissue mode to blood pulse mode, or vice-versa.

To transmit light from spectrometer 303 to the fingertip 379 of the patient, whose blood gases are being monitored, monitor 301 includes a source fiber optic bundle 373, which terminates at finger/fiber device 375. Receiving fiber optic 377 returns the light from finger/fiber holder 375 to fiber optic housing 331. Finger/fiber holder 375 allows transmission through finger 379 and allows for adequate holding of the finger.

In operation, multiple light emitting diode sources 311–325 emit light at discrete time intervals in the wavelength region between 500 and 2400 nm. The diodes are energized for time durations such that the necessary spectral information is recorded. This light is focused on the end of fiber optic interface 329, via focusing lenses 327 and then via source fiber 373 to illuminate the tissue, bone, nail and blood therein. A portion of the light which is transmitted through fingertip 379 is then returned to spectrometer 303 by fiber bundle 377. The returning light is then focused by focusing mirror 333 onto detector 335, capable of detecting wavelengths of light between 500 to 2400 nm.

The light intensities from the various diodes are then analyzed by processing unit 305 employing a appropriate algorithm. The instrument 301 can be operated in two different modes controlled by mode switch 371: (1) tissue determination mode; or (2) pulse blood mode. Instrument 301 will display the current values of pH, $PCO_2$, $[HCO_3^-]$, $PO_2$ and $O_2$ sat. as well as the past history of said analyte in trend displays 351–359. If a given analyte determination indicates that the analysis might be unreliable the outlier lights 361–369 will indicate such to the operator.

The number and selection of the light emitting diodes 311–325 will influence the instrumentation cost significantly. The selection of these diodes is determined by the above-described methodology including use of a genetic algorithm. The major cost parameters associated with such diode instrumentation are the number of diodes used, the wavelengths emitted by each of the diodes, and the resolution of each of the diodes. These parameters as well as performance are incorporated in the fitness function.

While the specification has focused primarily on the use of partial least squares as the multivariate analysis method of choice, those skilled in the art will appreciate that the wavelength selection, instrument design, and instrumentation will work with other multivariate algorithms. Multivariate algorithms used for quantitative spectroscopy can be divided globally into limited-wavelength and full spectrum. Examples of limited-wavelength are multiple linear regression (MLR), also known as inverse least squares, and ridge regression. Ridge regression has been used in non-medical situations in which the intensities at different spectral wavelengths exhibit significant collinearity. Martens and Naes, "Multivariate Calibration," John Wiley: Chichester, (1989), showed that ridge regression is mathematically similar to PCR, but cannot be described explicitly by data compression. Hoerl et al., "Practical use of ridge regression: a challenge met," Applied Statistics 34, 114–120, (1985), showed that ridge regression was a viable competitor to multiple linear regression in the context of predicting percent protein in wheat samples by using reflectance in the near infrared region. Naes et al., "Comparison of lineal statistical methods for calibration of NIR instruments", Applied Statistics 35, 195–206, (1985), concluded that ridge regression is a viable competitor to PLS and PCR when the number of spectral wavelengths approaches the number of calibration samples.

Examples of full spectrum methods are partial least squares (PLS), partial component regression (PCR), cross correlation, Kalman filtering, continuum regression and neural networks. A extensive discussion of multivariate methods for spectral analysis is available in Practical Fourier Transform Infrared Spectroscopy, chapter 8, "Methods applied to quantitative FT-IR analysis", copyright 1990, by David Haaland. Continuum regression comprises an infinite-member family of methods for multivariate calibration. PLS and PCR are individual members of the continuum regression family. See, M. Stone, and R. J. Brooks (1990), "Continuum Regression: Cross-validated Sequentially Constructed Prediction Embracing Ordinary Least Squares, Partial Least Squares and Principal Components Regression," Journal of the Royal Statistical Society B., 52, pp. 237–269.

Another type of multivariate algorithm gaining wide acceptance is a pattern recognition technique using what are called neural networks. Weights are applied to the inputs, which determine the signal strength. The sum of the inputs at each neuron determines the strength of the neuron. The weighted sum is transformed with a linear or nonlinear transfer function, the most popular transform function being the sigmoid function. This transfer function determines the output of the signal, depending on the gain that is set. All neurons are interconnected, but pass data only one way, as the brain does. The output signal can be transferred to several different neurons, each of which has its own weight. The network "learns" the weights of the output signal at each neuron, optimizing the weights to achieve the "correct responses" (i.e. the reference calibration values). Like other multivariate calibration methods, neural networks learn from the input they are given. They have the potential advantage that they can explicitly model nonlinearities. However, they also tend to be more susceptible to overfitting, and slower to compute, and are more difficult to interpret than PLS, PCR, and MLR.

Regardless of the full spectrum methods used, the difference between full spectrum and limited wavelength methods is significant. Limited-wavelength methods are not capable of using more wavelengths than samples. Full spectrum methods on the other hand are capable of using all independent sources of spectral information and are capable of using more wavelengths than samples. Thus, the methodology of wavelength selection and its capability to improve performance and decrease instrument cost can be applied to any multivariate algorithms. The exact multivariate algorithms used can be changed without affecting the scope of this invention.

Finally, it should be recognized that the wavelength region used for measurement will vary between the different analytes of interest. For example, acceptable accuracy results for bilirubin and hemoglobin are possible through use of the 300–1000 nm region. Specifically, bilirubin has a significant absorption peak at approximately 454 nm and oxygenated hemoglobin has a peak at approximately 410 nm. Alcohol, an analyte of significant interest, has a sharp spectral absorbance at 1190 nm. Oxygen saturation determination would be made in the range of 500–1000 nm, while blood-gas parameter determinations would be made in the range of 500–2400 nm.

What we claim is:

1. A method of determining non-invasively a concentration of a blood analyte in human tissue, said method including the steps of:
   a. irradiating said human tissue having unknown blood analyte concentration with electromagnetic energy including at least several wavelengths so that there is differential absorption of at least some of said wavelengths by said irradiated tissue as a function of said wavelengths and said blood analyte concentration, said differential absorption causing intensity variations of said wavelengths incident from said irradiated tissue;
   b. measuring the intensities of said wavelengths incident from said irradiated tissue;
   c. calculating said blood analyte concentration in said irradiated tissue from said measured intensities utilizing an algorithm and a model, said algorithm being capable of utilizing more of said measured intensities than calibration samples in which said blood analyte concentration is known, said model using selected wavelength subsets, said wavelength subsets comprising one or more of said wavelengths, said wavelength subsets are not systematically spaced, but are irregularly defined regions of the spectrum being used for analysis.

2. The method as set forth in claim 1, wherein the selection of said set of wavelength subsets is made independent of the knowledge of the spectral features of said irradiated tissue.

3. The method as set forth in claim 1, wherein said wavelength subsets are selected from wavelengths of light in the visible and infrared wavelength region by a multivariate search method for their predictive and synergistic ability to model the relationship between spectral information and known values of said blood analyte.

4. The method as set forth in claim 3, wherein said wavelength subset selection process is made utilizing a genetic algorithm.

5. The method as set forth in claim 1, wherein said algorithm is selected from the group including PLS, PLS2, PCR, CLS, Q-matrix, cross-correlation, Kalman filtering, neural networks, and continuum regression.

6. The method as set forth in claim 1 wherein the blood analyte is selected from the group including glucose, alcohol, ketones, fatty acids, cholesterol, lipoproteins, triglycerides, white blood cells, hematocrit, hemoglobin, blood urea nitrogen, creatinine, bilirubin, and electrolytes.

7. Apparatus for determining non-invasively a concentration of a blood analyte in human tissue, said apparatus comprising:

a. means for irradiating said human tissue having unknown blood analyte concentration with electromagnetic energy including at least several wavelengths so that there is differential absorption of at least some of said wavelengths by said irradiated tissue as a function of said wavelengths and said blood analyte concentration, said differential absorption causing intensity variations of said wavelengths incident from said irradiated tissue;

b. means for measuring the intensities of said wavelengths from said irradiated tissue;

c. means for calculating said blood analyte concentration in said irradiated tissue from said measured intensities utilizing an algorithm and a model, said algorithm also being capable of utilizing more of said measured intensities than than calibration samples in which said blood analyte concentration is known, said model using selected wavelength subsets, said wavelength subsets comprising one or more of said wavelengths, said wavelength subsets are not systematically spaced, but are irregularly defined regions of the spectrum being used for analysis.

* * * * *